US012000840B2

(12) United States Patent
Mao

(10) Patent No.: US 12,000,840 B2
(45) Date of Patent: *Jun. 4, 2024

(54) METHODS FOR DE NOVO PROTEIN SEQUENCING

(71) Applicant: Regeneron Pharmaceuticals, Inc., Tarrytown, NY (US)

(72) Inventor: Yuan Mao, Hartsdale, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 448 days.

This patent is subject to a terminal disclaimer.

(21) Appl. No.: 17/327,889

(22) Filed: May 24, 2021

(65) Prior Publication Data

US 2021/0278414 A1 Sep. 9, 2021

Related U.S. Application Data

(63) Continuation of application No. 16/542,788, filed on Aug. 16, 2019, now Pat. No. 11,047,863.

(Continued)

(51) Int. Cl.
*G01N 33/68* (2006.01)
*C07K 16/06* (2006.01)
(Continued)

(52) U.S. Cl.
CPC ....... *G01N 33/6851* (2013.01); *C07K 16/065* (2013.01); *G16B 20/00* (2019.02); *G16B 40/10* (2019.02); *H01J 49/305* (2013.01)

(58) Field of Classification Search
None
See application file for complete search history.

(56) References Cited

U.S. PATENT DOCUMENTS 5,824,556 A 10/1998 Tarr
7,642,509 B2 1/2010 Hartmer et al.
(Continued)

FOREIGN PATENT DOCUMENTS

AU 2012261953 A1 * 12/2013 ....... G01N 33/57411
CN 101298611 A 11/2008
(Continued)

OTHER PUBLICATIONS

International Search Report PCT Application No. PCT/US2019/046821, International Filing Date Aug. 16, 2019, dated Jan. 20, 2020.

(Continued)

*Primary Examiner* — Andrew Smyth
(74) *Attorney, Agent, or Firm* — Kramer Levin Naftalis & Frankel LLP

(57) ABSTRACT

A method for determining an amino acid sequence of a polypeptide, including comprising: contacting a first sample containing the polypeptide with a first protease (e.g., Trypsin) to produce a first set of digested peptide fragments; fragmenting the first set of digested peptide fragments to produce a first set of fragmented peptide ions; determining masses of the first set of fragmented peptide ions; contacting a second sample containing the polypeptide with a second protease (e.g., Tryp-N); fragmenting the second set of digested peptide fragments to produce a second set of fragmented peptide ions; selecting pairs of peptide ions from the first and the second set of fragmented peptide ions that differ in mass by a mass of an arginine amino acid residue or a lysine amino acid residue; assigning an ion type (either N-terminal peptide ion or C-terminal peptide ion) to the selected pairs of the peptide ions from two sets of fragmented peptide ions; selecting a mass ladder of the same-type peptide ions in either set of fragmented peptide ions (Continued)

with incremental mass by the mass of amino acid residue(s), and assembling the identified amino acid residues from the mass ladder to determine the amino acid sequence of the polypeptide of interest.

19 Claims, 23 Drawing Sheets

Specification includes a Sequence Listing.

Related U.S. Application Data

(60) Provisional application No. 62/719,292, filed on Aug. 17, 2018.

(51) Int. Cl.
*G16B 20/00* (2019.01)
*G16B 40/10* (2019.01)
*H01J 49/30* (2006.01)

(56) References Cited

U.S. PATENT DOCUMENTS

| | | | | |
|---|---|---|---|---|
| 8,338,122 | B2* | 12/2012 | Heck | G01N 33/6818 435/18 |
| 8,352,193 | B2 | 1/2013 | Schneider et al. | |
| 9,719,078 | B1* | 8/2017 | Pappin | C12N 9/58 |
| 11,047,863 | B2* | 6/2021 | Mao | G01N 33/6848 |
| 2004/0185448 | A1 | 9/2004 | Lopez-Avila et al. | |
| 2010/0301206 | A1 | 12/2010 | Brown et al. | |
| 2010/0311098 | A1* | 12/2010 | Heck | G01N 33/6818 435/23 |
| 2019/0352343 | A1 | 11/2019 | Squire et al. | |

FOREIGN PATENT DOCUMENTS

| | | |
|---|---|---|
| CN | 106414733 A | 2/2017 |
| CN | 107110840 A | 8/2017 |
| JP | 2007-322293 A | 12/2007 |
| JP | 2011-112562 A | 6/2011 |
| JP | 6281349 B2 | 2/2018 |
| WO | WO 2017/022562 A1 | 2/2017 |

OTHER PUBLICATIONS

Brownstein, C. Naomi et al., "Paired single residue-transposed Lys-N and Lys-C digestions for label-free identification of N-terminal and C-terminal MS/MS peptide product ions:ultrahigh resolution Fourier transform ion cyclotron resonance mass spectrometry and tandem mass spectrometry for peptidede novo sequencing" Rapid Commun. Mass Spectrom. 2015, 29, 659-666 (wiley online library.com) DOI: 10.1002/rcm.7137.

Search Reporting issued for corresponding Singapore Application No. 11202100740Y dated Jul. 26, 2022.

Written Report issued for corresponding Singapore Application No. 11202100740Y dated Jul. 28, 2022.

* cited by examiner

FIG. 1A

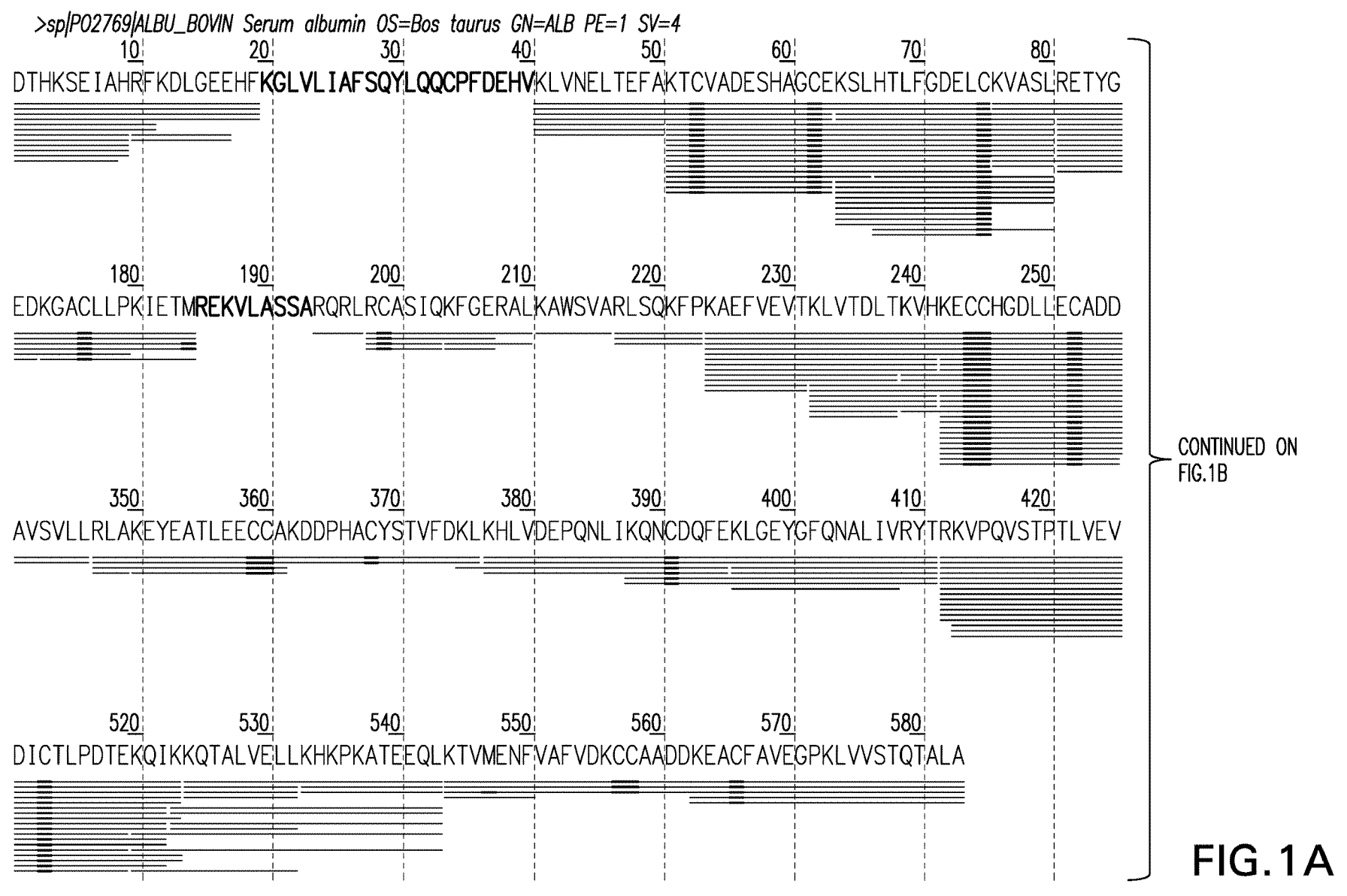

>sp|P02769|ALBU_BOVIN Serum albumin OS=Bos taurus GN=ALB PE=1 SV=4

DTHKSEIAHRFKDLGEEHFKGLVLIAFSQYLQQCPFDEHVKLVNELTEFAKTCVADESHAGCEKSLHTLFGDELCKVASLRETYG

EDKGACLLPKIETMREKVLASSARQRLRCASIQKFGERALKAWSVARLSQKFPKAEFVEVTKLVTDLTKVHKECCHGDLLECADD

AVSVLLRLAKEYEATLEECCAKDDPHACYSTVFDKLKHLVDEPQNLIKQNCDQFEKLGEYGFQNALIVRYTRKVPQVSTPTLVEV

DICTLPDTEKQIKKQTALVELLKHKPKATEEQLKTVMENFVAFVDKCCAADDKEACFAVEGPKLVVSTQTALA

```
 90       100       110       120       130       140       150       160       170
DMADCCEKQEPERNECFLSHKDDSPDLPKLKPDPNTLCDEFKADEKKFWGKYLYEIARRHPYFYAPELLYYANKYNGVFQECCQA 260       270       280       290       300       310       320       330       340
RADLAKYICDNQDTISSKLKECCDKPLLEKSHCIAEVEKDAIPENLPPLTADFAEDKDVCKNYQEAKDAFLGSFLYEYSRRHPEY 430       440       450       460       470       480       490       500       510
SRSLGKVGTRCCTKPESERMPCTEDYLSLILNRLCVLHEKTPVSEKVTKCCTESLVNRRPCFSALTPDETYVPKAFDEKLFTFHA
```

(SEQ ID NO: 1)

CONTINUED FROM FIG. 1A

FIG. 2B

METHODS FOR DE NOVO PROTEIN SEQUENCING

CROSS-REFERENCE TO RELATED APPLICATIONS

This application is a continuation of U.S. patent application Ser. No. 16/542,788, filed on Aug. 16, 2019 which claims the benefit of U.S. Provisional Application No. 62/719,292, filed Aug. 17, 2018, which is incorporated herein by reference in its entirety.

REFERENCE TO A SEQUENCE LISTING

This application incorporates by reference the Sequence Listing submitted in Computer Readable Form as file 10478US01-Sequence.txt, created on Aug. 16, 2019 and containing 7,747 bytes.

FIELD OF THE INVENTION

The present invention pertains to biopharmaceuticals, and relates to the do novo determination of protein or polypeptide sequences.

BACKGROUND

Protein sequencing has traditionally relied on the sequential detection of individually cleaved N-terminal amino acids using Edman degradation chemistry and the detection and identification of the different amino acid Edman derivatives, for example, using techniques such as differential HPLC retention and UV absorption. More recently, mass spectrometry has been used to sequence and/or identify proteins or polypeptides with increased speed, accuracy and sensitivity. However, these methods are generally low-throughput and still rely on Edman degradation. While dramatic improvements have been made in high-throughput massively parallel DNA sequencing platforms capable of sequencing large numbers of different nucleic acid molecules simultaneously, advances in mass spectrometer performance have been incremental. Relatively little progress has been made towards the development of "next generation" platforms for global protein sequencing at the individual single amino acid residue level.

Accordingly, there remains a need for novel methods and assays for sequencing single polypeptide.

BRIEF SUMMARY OF THE INVENTION

In one aspect, the present invention provides a method for the de novo determination of an amino acid sequence of a polypeptide of interest, in which the method includes: contacting a first sample containing the polypeptide of interest with a first protease that cleaves peptide bonds after a basic amino acid under conditions that permit the first protease to digest the polypeptide of interest to produce a first set of digested peptide fragments; fragmenting the first set of digested peptide fragments to produce a first set of fragmented peptide ions corresponding to peptides in the first set of digested peptide fragments; determining masses of the first set of fragmented peptide ions; contacting a second sample containing the polypeptide of interest with second protease that cleaves peptide bonds before a basic amino acid, under conditions that permit the second protease to digest the polypeptide of interest to produce a second set of digested peptide fragments; fragmenting the second set of digested peptide fragments to produce a second set of fragmented peptide ions corresponding to peptides in the second set of digested peptide fragments; determining masses of the second set of fragmented peptide ions; selecting pairs of peptide ions from the first set of fragmented peptide ions and the second set of fragmented peptide ions that differ in mass by a mass of an arginine amino acid or a mass of a lysine amino acid; assigning an ion type (either N-terminal peptide ion or C-terminal peptide ion) to the selected pairs of the peptide ions from two sets of fragmented peptide ions; selecting a mass ladder of the same-type peptide ions in either set of fragmented peptide ions with incremental mass by the mass of amino acid residue(s) and assembling the identified amino acid residues from the mass ladder of peptide ions to determine the amino acid sequence of the polypeptide of interest.

In some embodiments of the method, the first protease is Trypsin.

In some embodiments of the method, the second protease Tryp-N.

In some embodiments, the method further includes selecting a first digested peptide fragment from the first set of digested peptide fragments; and selecting a second digested peptide fragment from the second set of digested peptide fragments with a mass identical to the first digested peptide fragment.

In some embodiments, the method further includes selecting a first digested peptide fragment from the first set of digested peptide fragments; and selecting a second digested peptide fragment from the second set of digested peptide fragments with a mass that has a mass difference equal to the mass difference between a lysine amino acid residue and an arginine amino acid residue relative to the first digested peptide fragment.

In various embodiments of the method, assigning the pairs of fragmented peptide ions to derive amino acid sequences, includes: selecting a first digested peptide fragment from the first set of digested peptide fragments; fragmenting the first digested peptide fragment to produce a first series of fragmented peptide ions corresponding to the first digested peptide fragment; selecting a second digested peptide fragment from the second set of digested peptide fragments corresponding to the first digested peptide fragment; fragmenting the second digested peptide fragment to produce a second series of fragmented peptide ions corresponding to the second digested peptide fragment; assigning an ion type (either N-terminal peptide ion or C-terminal peptide ion) to the selected pairs of the peptide ions from two sets of fragmented peptide ions; selecting a mass ladder of the same-type peptide ions in either set of fragmented peptide ions with incremental mass by the mass of amino acid residue(s); and determining individual amino acid residues of the first and second digested peptide fragments from selected mass ladder of peptide ions to produce an amino acid sequence of the first and/or second fragmented peptide.

In various embodiments, the pairs of peptide ions from the first set of fragmented peptide ions and the second set of fragmented peptide ions are selected that differ in mass by the mass of an arginine amino acid residue. In various embodiments, a negative difference in mass of an arginine amino acid residue in the pairs of peptide ions from the first set of fragmented peptide ions and the second set of fragmented peptide ions indicates that the peptide has an N-terminal arginine residue. In various embodiments, a positive difference in mass of an arginine residue in the pairs of peptide ions from the first set of fragmented peptide ions and the second set of fragmented peptide ions indicates that the peptide has a C-terminal arginine residue. In various embodiments, the pairs of peptide ions from the first set of fragmented peptide ions and the second set of fragmented peptide ions are selected that differ in mass by the mass of a lysine amino acid residue. In embodiments, a negative difference in mass of a lysine amino acid residue in the pairs of peptide ions from the first set of fragmented peptide ions and the second set of fragmented peptide ions indicates that the peptide has an N-terminal lysine residue. In embodiments, a positive difference in mass of a lysine amino acid residue in the pairs of peptide ions from the first set of fragmented peptide ions and the second set of fragmented peptide ions indicates that the peptide has a C-terminal lysine residue.

In various embodiments of the method, the selected fragmented peptide ions from the first set of fragmented peptide ions correspond with the selected fragmented peptide ions from the second set of fragmented peptide ions.

In various embodiments of the method, the selected fragmented peptide ions from the first set of fragmented peptide ions are b ions and the selected fragmented peptide ions from the second set of fragmented peptide ions are b ions having a difference in mass of an arginine amino acid residue or a mass of a lysine amino acid residue.

In various embodiments of the method, the selected fragmented peptide ions from the first set of fragmented peptide ions are y ions and the selected fragmented peptide ions from the second set of fragmented peptide ions are y ions having a difference in mass of an arginine amino acid or a mass of a lysine amino acid.

In various embodiments of the method, mass is determined using mass spectrometry.

In various embodiments of the method, the fragment ions are produced using tandem mass spectrometry.

In various embodiments of the method, the polypeptide of interest comprises a protein.

In various embodiments of the method, the polypeptide of interest comprises an antibody, such as a monoclonal antibody, a monospecific antibody or a bispecific antibody.

DESCRIPTION OF THE FIGURES

FIGS. 1A and 1B show the bovine serum albumin (BSA) sequence coverage using a Tryp-N protease digestion. The sequence coverage is 91.4%. Various peptide fragments generated from a Tryp-N digest of BSA are shown below the BSA protein sequence (SEQ ID NO: 1).

FIGS. 2A and 2B show the BSA sequence coverage using a Trypsin protease digestion. The sequence coverage is 94.2%. Various peptide fragments generated from a Trypsin digest of BSA are shown below the BSA protein sequence (SEQ ID NO: 1)

FIG. 5A is an exemplary mass spectra of the peptide LVNELTEFAK (SEQ ID NO: 3) subjected to tandem mass spec showing the detected b and y ions. FIG. 5B is an exemplary mass spectra of the peptide KLVNELTEFA (SEQ ID NO: 4) subjected to tandem mass spec showing the detected b and y ions. FIG. 5C shows the generation of the primary sequence LVNELTEFA (SEQ ID NO: 5) using the determined ion maps for the Trypsin digest and the Tryp-N digest.

FIG. 7A is an exemplary mass spectra of the peptide HPEYAVSVLLR (SEQ ID NO: 7) subjected to tandem mass spec showing the detected b and y ions. FIG. 7B is an exemplary mass spectra of the peptide RHPEYAVSVLL (SEQ ID NO: 8) subjected to tandem mass spec showing the detected b and y ions. FIG. 7C shows the generation of the primary sequence HPEYAVSVLL (SEQ ID NO: 9) using the determined ion maps for the Trypsin digest and the Tryp-N digest.

FIG. 9A is an exemplary mass spectra of the peptide CCTESLVNR (SEQ ID NO: 11) subjected to tandem mass spec showing the detected b and y ions. FIG. 9B is an exemplary mass spectra of the peptide KCCTESLVN (SEQ ID NO: 12) subjected to tandem mass spec showing the detected b and y ions. FIG. 9C shows the generation of the primary sequence CCTESLVN (SEQ ID NO: 13) using the determined ion maps for the Trypsin digest and the Tryp-N digest.

FIG. 11A is an exemplary mass spectra of the peptide FKDLGEEHFK (SEQ ID NO: 15) subjected to tandem mass spec showing the detected b and y ions. FIG. 11B is an exemplary mass spectra of the peptide RFKDLGEEHF (SEQ ID NO: 16) subjected to tandem mass spec showing the detected b and y ions. FIG. 11C shows the generation of the primary sequence FKDL-GEEHF (SEQ ID NO: 17) using the determined ion maps for the Trypsin digest and the Tryp-N digest.

DETAILED DESCRIPTION OF THE INVENTION

Figure 2A:
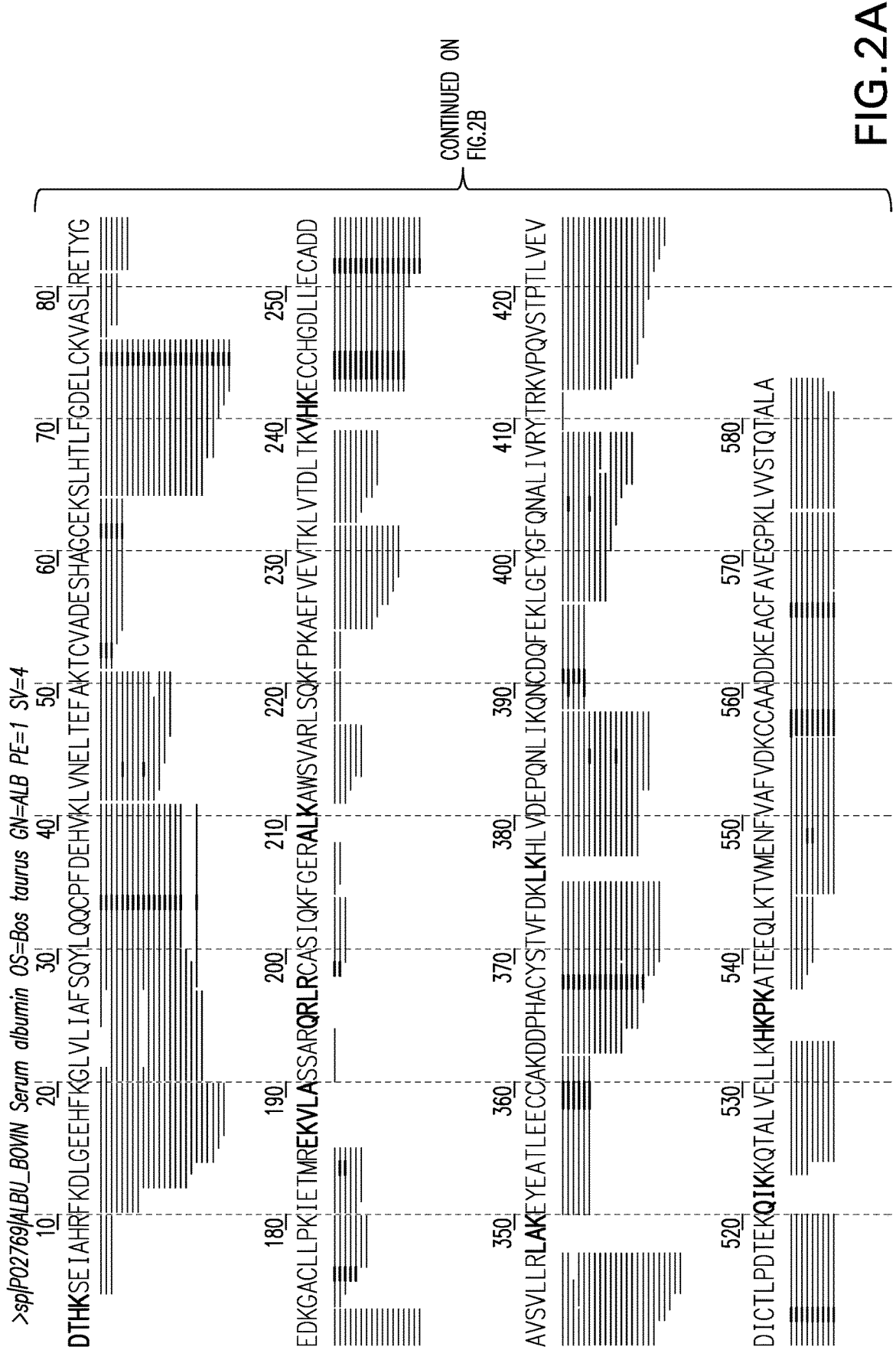

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.)

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein

MS/MS: Tandem Mass Spectrometry
mAb: Monoclonal Antibody
IgG: Immunoglobulin G
LC: Light Chain
HC: Heavy Chain
MS: Mass Spectrometry

Definitions

The term "antibody", as used herein, is intended to refer to immunoglobulin molecules comprised of four polypeptide chains, two heavy (H) chains and two light (L) chains interconnected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains,* 27(1) Dev. Comp. Immunol. 55-77 (2003); and M. Potter, *Structural correlates of immunoglobulin diversity,* 2(1) Surv. Immunol. Res. 27-42 (1983).

The term antibody also encompasses a "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989).

The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "sample," as used herein, refers to a mixture of molecules that comprises at least an polypeptide of interest, such as a monoclonal antibody, that is subjected to manipulation in accordance with the methods of the invention, including, for example, separating, analyzing, extracting, concentrating or profiling.

The terms "analysis" or "analyzing," as used herein, are used interchangeably and refer to any of the various methods of separating, detecting, isolating, purifying, solubilizing, detecting and/or characterizing molecules of interest (e.g., polypeptides, such as monoclonal antibodies). Examples include, but are not limited to, solid phase extraction, solid phase micro extraction, electrophoresis, mass spectrometry, e.g., tandem mass spectrometry, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, nuclear magnetic resonance, infrared analysis, flow injection analysis, capillary electrochromatography, ultraviolet detection, and combinations thereof.

"Chromatography," as used herein, refers to the process of separating a mixture, for example a mixture containing peptides, proteins, polypeptide and/or antibodies, such as monoclonal antibodies. It involves passing a mixture through a stationary phase, which separates molecules of interest from other molecules in the mixture and allows one or more molecules of interest to be isolated. Examples of methods of chromatographic separation include capillary-action chromatography, such as paper chromatography, thin layer chromatography (TLC), column chromatography, fast protein liquid chromatography (FPLC), nano-reversed phase liquid chromatography, ion exchange chromatography, gel chromatography, such as gel filtration chromatography, size exclusion chromatography, affinity chromatography, high performance liquid chromatography (HPLC), hydrophilic interaction liquid chromatography (HILIC), and reverse phase high performance liquid chromatography (RP-HPLC) amongst others.

"Contacting," as used herein, includes bringing together at least two substances in solution or solid phase, for example contacting a sample with a protease.

The term "corresponding" is a relative term indicating similarity in position, purpose or structure, and may include peptides of identical structure but for the presence or absence of an arginine or lysine amino acid residue on the N- or C-terminus. In some embodiments, mass spectral signals in a mass spectrum that are due to corresponding peptides of identical structure but for the presence or absence of an arginine or lysine amino acid residue on the N- or C-terminus are "corresponding" mass spectral signals. A mass spectral signal due to a particular peptide is also referred to as a signal corresponding to the peptide. In certain embodiments, a particular peptide sequence or set of amino acids can be assigned to a corresponding peptide mass.

The terms "fragment peptide" or "peptide fragment," as used herein, refer to a peptide that is derived from the full length polypeptide, such as a protein and/or monoclonal antibody, through processes including fragmentation, enzymatic proteolysis, or chemical hydrolysis. Such proteolytic peptides include peptides produced by treatment of a protein with one or more proteases such as Trypsin or Tryp-N. A fragment peptide, or peptide fragment, can be a digested peptide.

The term "isolated," as used herein, refers to a biological component (such as a nucleic acid, peptide, protein, lipid, or metabolite) that has been substantially separated, produced apart from, or purified away from other biological components in the cell of the organism in which the component naturally occurs or is transgenically expressed, that is, other chromosomal and extrachromosomal DNA and RNA, proteins, lipids, and metabolites. Nucleic acids, peptides, proteins, lipids and metabolites which have been "isolated" thus include nucleic acids, peptides, proteins, lipids, and metabolites purified by standard or non-standard purification methods. The term also embraces nucleic acids, peptides, proteins, lipids, and metabolites prepared by recombinant expression in a host cell as well as chemically synthesized peptides, lipids, metabolites, and nucleic acids.

"Mass spectrometry" is a method wherein, a sample is analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), orbitrap mass analyzer, Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example, one or more dimensions of liquid or size exclusion chromatography.

Tandem mass spectrometry or MS/MS is a technique to break down selected ions (precursor ions) into fragments (product ions). The fragments then reveal aspects of the chemical structure of the precursor ion. In tandem mass spectrometry, once samples are ionized (for example by ESI, MALDI, EI, etc.) to generate a mixture of ions, precursor ions, for example peptides from a digest, of a specific mass-to-charge ratio (m/z) are selected (MS1) and then fragmented (MS2) to generate a product ions for detection. Typical Tandem MS instruments include QqQ, QTOF, and hybrid ion trap/FTMS, etc. One example of an application of tandem mass spectrometry is protein identification. The first mass analyzer isolates ions of a particular m/z value that represent a single species of peptide among many introduced into and then emerging from the ion source. Those ions are then accelerated into a collision cell containing an inert gas such as argon to induce ion fragmentation. This process is designated collisionally induced dissociation (CID) or collisionally activated dissociation (CAD). The m/z values of fragment ions are then measured in a $2^{nd}$ mass analyzer to obtain amino acid sequence information. Tandem mass spectrometry can be used to identify the sequence of a peptide and hence full or partial length proteins according to the methods disclosed herein. A notation has been developed for indicating peptide fragments that arise from a tandem mass spectrum. As used herein peptide fragment ions are indicated by b if the charge is retained on the N-terminus and by a y if the charge is maintained on the C-terminus. The number following the b or y indicates the number of amino acids in the fragment. Precursor ions can be activated (with increased internal energy) in many different ways. Fragmentation patterns depend on how energy is transferred to the precursor ion, the amount of energy transferred, and how the transferred energy is internally distributed. Collision-induced dissociation and infrared multiphoton dissociation are "slow-heating" techniques that increase the Boltzmann temperature of the ion and thus preferentially cleave the weakest bonds to produce mainly b and y ions.

The terms "peptide," "protein" and "polypeptide" refer, interchangeably, to a polymer of amino acids and/or amino acid analogs that are joined by peptide bonds or peptide bond mimetics. The twenty naturally-occurring amino acids and their single-letter and three-letter designations are as follows: Alanine A Ala; Cysteine C Cys; Aspartic Acid D Asp; Glutamic acid E Glu; Phenylalanine F Phe; Glycine G Gly; Histidine H His; Isoleucine I Ile; Lysine K Lys; Leucine L Leu; Methionine M Met; Asparagine N Asn; Proline P Pro; Glutamine Q Gin; Arginine R Arg; Serine S Ser; Threonine T Thr; Valine V Val; Tryptophan w Trp; and Tyrosine Y Tyr.

References to a mass of an amino acid means the monoisotopic mass or average mass of an amino acid at a given isotopic abundance, such as a natural abundance. In some examples, the mass of an amino acid can be skewed, for example, by labeling an amino acid with an isotope. Some degree of variability around the average mass of an amino acid is expected for individual single amino acids based on the exact isotopic composition of the amino acid. The masses, including monoisotopic and average masses for amino acids are easily obtainable by one of ordinary skill the art.

Similarly, references to a mass of a peptide means the monoisotopic mass or average mass of a peptide at a given isotopic abundance, such as a natural abundance. In some examples, the mass of a peptide can be skewed, for example, by labeling one or more amino acids in the peptide with an isotope. Some degree of variability around the average mass of a peptide is expected for individual single peptides based on the exact isotopic composition of the peptide. The mass of a particular peptide can be determined by one of ordinary skill the art.

General Description

Figure 2B:
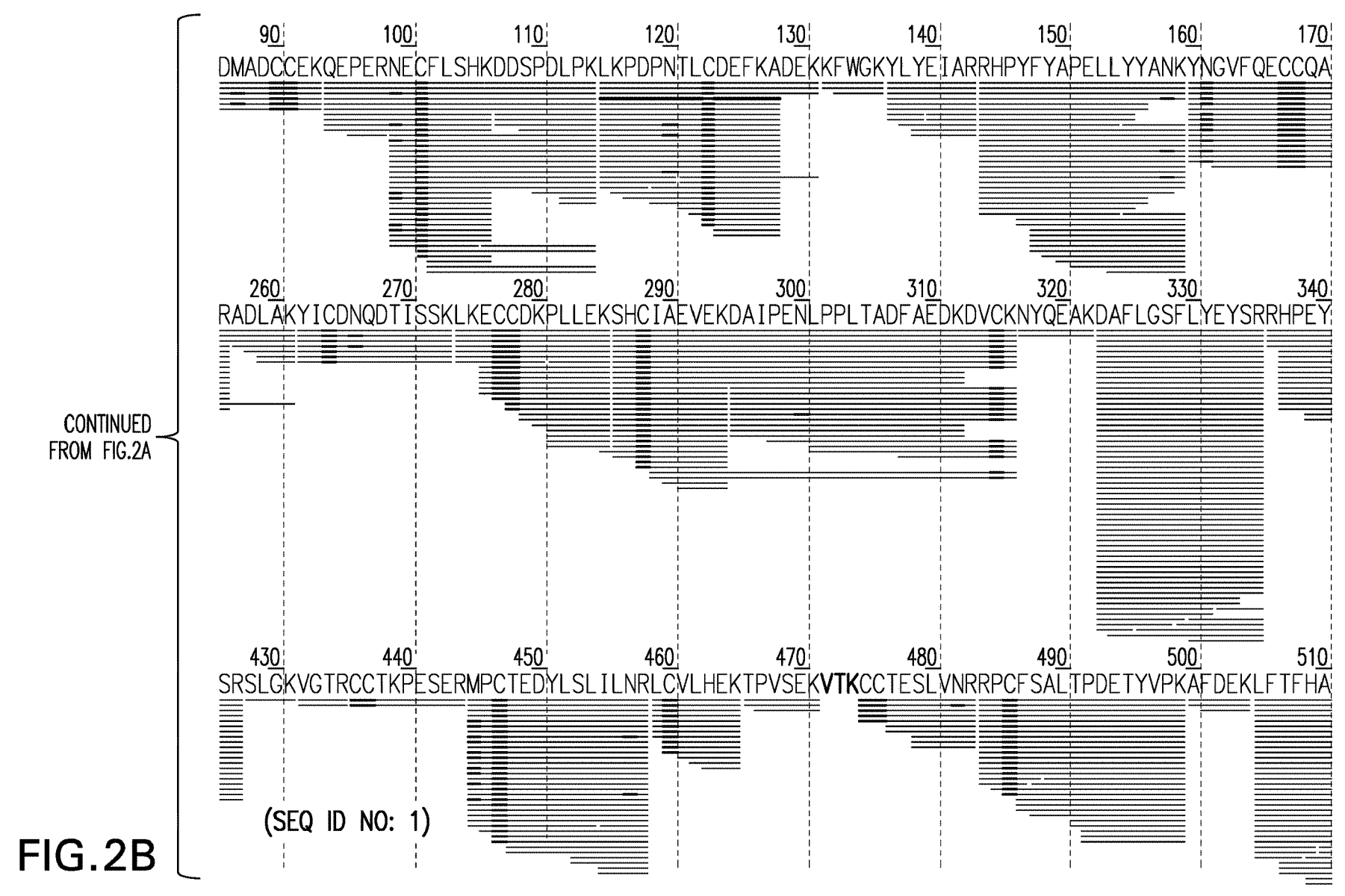
Figure 12:
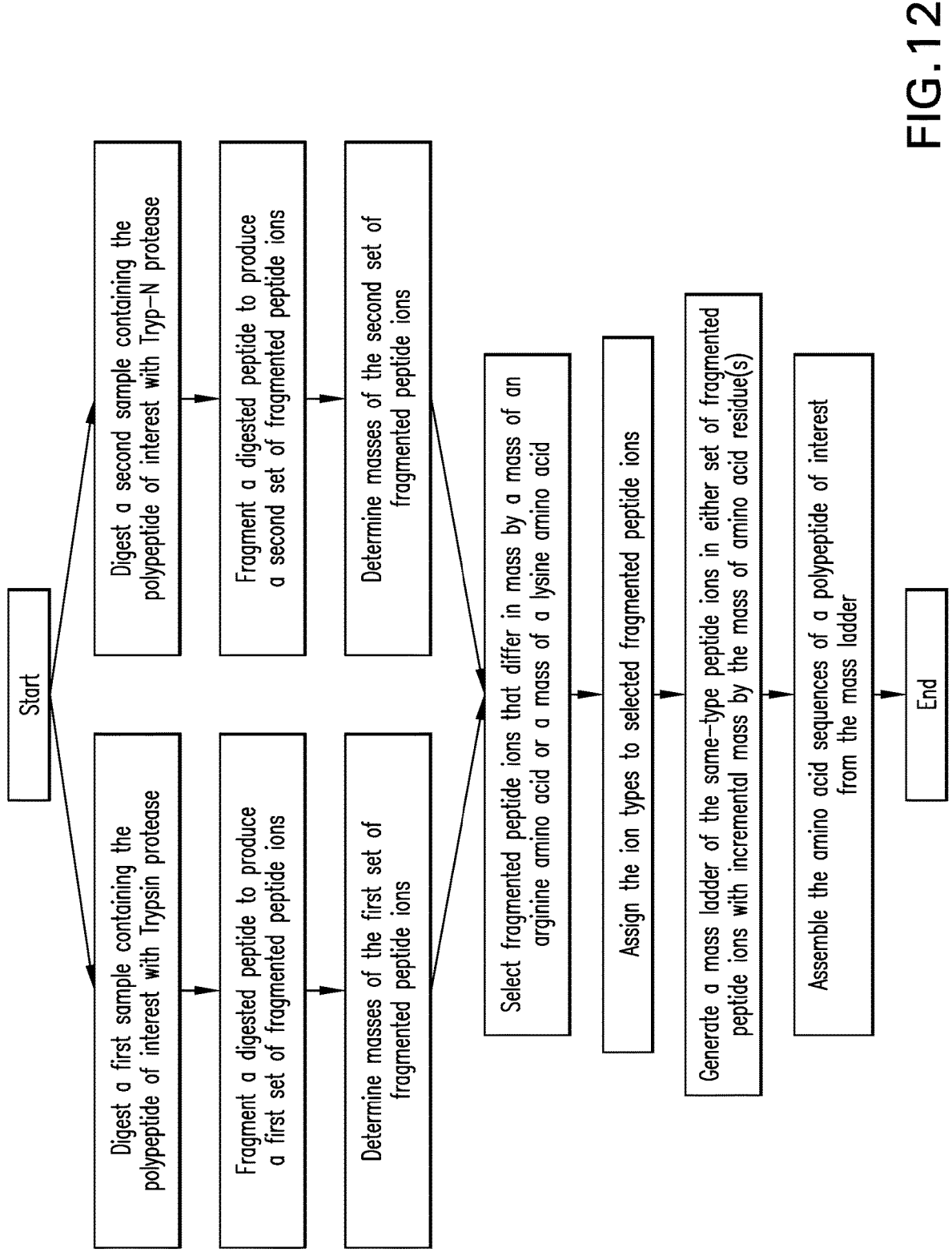
FIG. 12 is a block diagram depicting a method for determining the sequence of a polypeptide, in accordance with certain exemplary embodiments.

Aspects of the present disclosure concern a method for determining the amino acid sequence of a polypeptide of interest, such as a monoclonal antibody or other protein of interest. Much like DNA sequencing, the disclosed method requires no prior information about the sequence of the polypeptide. For reference, FIG. 12 depicts an exemplary, although not limiting, work-flow for the disclosed method. One of the unique features of the disclosed method is the use of a pair of proteases that cut or cleave peptide bonds before and after a basic amino acid, respectively. The first protease, such as Trypsin, cleaves the peptide bond immediately after a basic amino acid, such as after an arginine or lysine residue, while the second protease, such as Tryp-N, cleaves the peptide bond immediately before the a basic amino acid, such as before an arginine or lysine residue (maps of the peptides produced in a bovine serum albumin digest by each protease are shown in FIGS. 1 and 2). The inventors recognized that such a set of proteases could be used with mass spectrometry techniques to determine the sequence of a polypeptide that has been digested with the two enzymes separately.

Thus, disclosed herein is a method of determining an amino acid sequence of a polypeptide of interest. In embodiments of the method, a sample, such as a first sample, containing a polypeptide of interest (for example of unknown sequence) is contacted with the first protease under conditions that permit the first protease to digest the polypeptide of interest and produce digested peptide fragments, for example, a first set of digested peptide fragments. The digest may be a complete digest or an incomplete digest, for example, to produce overlapping fragments. In embodiments in parallel, such as concurrently, or sequentially in any order, a sample, such as a second sample split from the first sample, containing the polypeptide of interest is contacted with the second protease, such as Tryp-N, protease under conditions that permit the second protease to digest the polypeptide of interest, and produce digested peptide fragments, for example, a second set of digested peptide fragments. The digest may be a complete digest or an incomplete digest, for example, to produce overlapping fragments.

Figure 3:
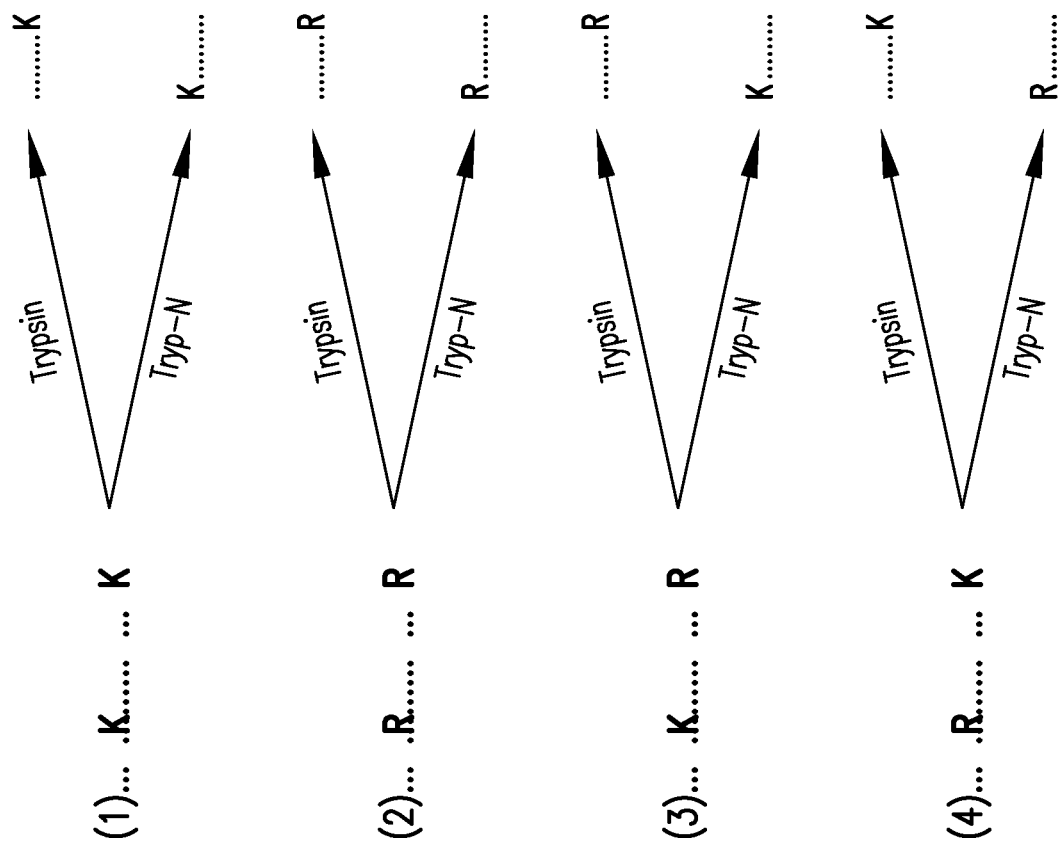
FIG. 3 shows the resulting peptide fragments generated from digests of model polypeptides by Tryp-N protease and Trypsin protease. The four different primary protein sequence patterns are considered.

FIG. 3 depicts the digested peptide fragments generated for a portion of a polypeptide that is bounded by two basic amino acids, such as bounded by a lysine residue and/or an arginine residue as indicated. As shown in FIG. 3, eight species may be generated (four for each enzyme) that are bounded either at the N- or C-terminus by a lysine residue or an arginine residue as shown. In case (1), the peptide sequence (in the context of a larger peptide or protein) is bounded on the N- and C-terminal ends by lysine (K) amino acid residues. Digestion by Trypsin protease results in fragment peptides having a C-terminal lysine amino acid residue, because the Trypsin protease cuts the peptide chain after (i.e., C-terminal to) lysine amino acids. Digestion by Tryp-N protease results in fragment peptides having an N-terminal lysine amino acid residue, because the Tryp-N protease cuts the peptide chain before (i.e., N-terminal to) lysine amino acids. In case (2), the peptide sequence (in the context of a larger peptide or protein) is bounded on the N- and C-terminal ends by arginine (R) amino acid residues. Digestion by Trypsin protease results in fragment peptides having a C-terminal arginine amino acid residue, because the Trypsin protease cuts the peptide chain before (i.e., C-terminal to) arginine amino acids. Digestion by Tryp-N protease results in fragment peptides having an N-terminal arginine amino acid residue, because the Tryp-N protease cuts the peptide chain before (i.e., N-terminal to) arginine amino acids. In case (3), the peptide sequence (in the context of a larger peptide or protein) is bounded on the N-terminal end by a lysine amino acid residue and on the C-terminal end by an arginine amino acid residue. Digestion by Trypsin protease results in fragment peptides having a C-terminal arginine amino acid residue. Digestion by Tryp-N protease results in fragment peptides having an N-terminal lysine amino acid residue. In case (4), the peptide sequence (in the context of a larger peptide or protein) is bounded on the N-terminal end by an arginine amino acid residue and the C-terminal end by a lysine amino acid residue. Digestion by Trypsin protease results in fragment peptides having a C-terminal lysine amino acid residue. Digestion by Tryp-N protease results in fragment peptides having an N-terminal arginine amino acid residue.

The inventors recognized that during fragmentation, for example, in a tandem mass spectrometer, that the b and y ions produced from the individual digested peptide fragments (see cases 1-4 discussed above) would differ in the mass by either the mass of an arginine amino acid residue or a lysine amino acid residue depending on whether they had been digested by Trypsin or Tryp-N. They further recognized that this difference could be exploited to determine N-terminal or C-terminal ion type for fragment ions and assemble amino acid residues identified from a mass ladder of the same-type fragment ions with incremental mass by the mass of amino acid residue(s) into specific sequences of peptides and that these peptide sequences could themselves be assembled into a full length amino acid sequence of a polypeptide, such as a monoclonal antibody. Table 1 shows the difference in mass for b and y fragment ions for the Trypsin digest and the Tryp-N digest by subtracting the mass of the specified Tryp-N fragment ion from the mass of the specified Trypsin fragment ion.

TABLE 1

Difference in Mass for b and y Fragment Ions.

| Sequence | Trypsin | Tryp-N | Difference |
|---|---|---|---|
| | | Case 1 | |
| K . . . K | b(x) − | b(x + 1) | −K |
| | y(x) − | y(x − 1) | +K |
| | | Case 2 | |
| R . . . R | b(x) − | b(x + 1) | −R |
| | y(x) − | y(x − 1) | +R |
| | | Case 3 | |
| K . . . R | b(x) − | b(x + 1) | −K |
| | y(x) − | y(x − 1) | +R |
| | | Case 4 | |
| R . . . K | b(x) − | b(x + 1) | −R |
| | y(x) − | y(x − 1) | +K |

By way of example, for case (1), the mass of a b6 fragment ion from the Trypsin digest, less the mass of a b7 fragment ion from the Tryp-N digest, would result in a mass that was negative the mass of a lysine residue. Alternatively, subtraction of the mass of a b6 fragment ion from the Trypsin digest from the mass of a b7 fragment ion from the Tryp-N digest would result in a mass that was positive the mass of a lysine residue. Likewise, the mass of a y6 fragment ion from the Trypsin digest, less the mass of a y5 fragment ion from the Tryp-N digest, would result in a mass that was positive the mass of a lysine residue. Alternatively, subtraction of the mass of a y6 fragment ion from the Trypsin digest from the mass of a y5 fragment ion from the Tryp-N digest would result in a mass that was negative the mass of a lysine residue.

In embodiments, the digested peptide fragments from the first protease digest, for example, the first set of digested peptide fragments, are fragmented to produce a first set of fragmented peptide ions, for example using a tandem mass spectrometer. The masses of the first set of fragmented peptide ions are then determined, for example by mass spectrometry. In embodiments, the digested peptide fragments from the second protease digest, for example, a second set of digested peptide fragments, are fragmented to produce a second set of fragmented peptide ions, for example using a tandem mass spectrometer. The masses of the second set of fragmented peptide ions is then determined, for example by mass spectrometry. Using the masses of the first and second sets of fragmented peptide ions, corresponding pairs of peptide ions from the first set of fragmented peptide ions and the second set of fragmented peptide ions are selected that differ in mass by a mass of an arginine amino acid residue or a mass of a lysine amino acid residue. By corresponding pairs of peptide ions it is meant to mean one selected from the first set and one selected from the second set. In embodiments, the ion type is determined from pairs of peptide ions selected from the fragmented peptide ions and a mass ladder of the same-type peptide ions with the incremental mass by the mass of amino acid residue(s) from either the first set of fragmented peptide ions or the second set of fragmented peptide ions is generated. By examining the mass difference of two adjacent peptide ions in the mass ladder to the mass of the individual 20 amino acids one of ordinary skill in the art can determine the individual amino acids that make up particular fragmented peptide ions. In certain embodiments, by using multiple fragmented peptide ions that correspond to a particular digested peptide, for example a b series of fragmented peptide ions and/or a y series of fragmented peptide ions (e.g. b1, b2, b3, b4, b5, etc. or y1, y2, y3, y4, etc.) the primary sequence of a particular digested peptide can be determined with high confidence. The assembly of peptides from mass spectrometry produced ion maps in cases 1-4, as discussed above, is shown in FIGS. 4-11C. In some embodiments of the method, assigning the pairs of fragmented peptide ions to derive amino acid sequences includes: selecting a first digested peptide fragment from the first set of digested peptide fragments; fragmenting the first digested peptide fragment to produce a first series of fragmented peptide ions corresponding to the first digested peptide fragment; selecting a second digested peptide fragment from the second set of digested peptide fragments corresponding to the first digested peptide fragment; fragmenting the second digested peptide fragment to produce a second series of fragmented peptide ions corresponding to the second digested peptide fragment; determining the ion type for selected pairs of peptide ions from the two series of fragmented peptide ions; selecting a mass ladder of the same-type peptides ions with the incremental mass by the mass of amino acid residue(s) from either set of fragmented peptide ions and determining individual amino acid residues of the first and second digested peptide fragment from the mass ladder of peptide ions to produce an amino acid sequence of the first and/or second fragmented peptide. Once the amino acid sequence of the peptides in the digest are determined, or a fraction thereof, the assigned amino acid sequences of the peptides may be assembled to form the amino acid sequence of the polypeptide of interest, for example using a sequence alignment of overlapping or partially overlapping sequences, see for example FIGS. 1 and 2 for BSA.

In some embodiments, the method includes selecting a first digested peptide fragment from the first set of digested peptide fragments, and selecting a second digested peptide fragment from the second set of digested peptide fragments with a mass identical to the first digested peptide fragment (see case (1) and (2) in FIGS. 4-7C). In embodiments, the method includes selecting a first digested peptide fragment from the first set of digested peptide fragments and selecting a second digested peptide fragment from the second set of digested peptide fragments with a mass that has a mass difference equal to the mass difference between a lysine amino acid residue and a arginine amino acid residue from the first digested peptide fragment (see case (3) and (4) in FIGS. 8-11C). In embodiments, the method includes selecting a first fragmented peptide from the first set of fragment peptides and fragmenting the selected fragmented peptide to produce fragmented peptide ions corresponding to the selected fragmented peptide. In embodiments, the first fragmented peptide ions are assigned an amino acid sequence based on the mass of the fragmented peptide ions. In embodiments, a mass ladder of the same-type peptide ions with the incremental mass by the mass of amino acid residue(s) is generated in each set of fragmented peptide ions. In embodiments, individual amino acid residues identified from either the first set of fragmented peptide ions or the second set of fragmented peptide ions are assembled to produce an amino acid sequence of the first and/or second fragmented peptide.

In certain embodiments, the method includes selecting pairs of peptide ions from the first set of fragmented peptide ions and the second set of fragmented peptide ions that differ in mass by the mass of an arginine amino acid residue. In certain embodiments, a negative difference in mass of an arginine amino acid residue between a peptide ion from the first set of fragmented peptide ions and a peptide ion from the second set of fragmented peptide ions indicates that the peptide has an N-terminal arginine residue. In certain embodiments, a positive difference in mass of an arginine amino acid residue between a peptide ion from the first set of fragmented peptide ions and a peptide ion from the second set of fragmented peptide ions indicates that the peptide has a C-terminal arginine residue. In certain embodiments, the method includes selecting pairs of peptide ions from the first set of fragmented peptide ions and the second set of fragmented peptide ions that differ in mass by the mass of a lysine amino acid residue. In certain embodiments, a negative difference in mass of a lysine amino acid residue between a peptide ion from the first set of fragmented peptide ions and a peptide ion from the second set of fragmented peptide ions indicates that the peptide has an N-terminal lysine residue. In certain embodiments, a positive difference in mass of a lysine amino acid residue between a peptide ion from the first set of fragmented peptide ions and a peptide ion from the second set of fragmented peptide ions indicates that the peptide has a C-terminal lysine residue. In certain embodiments, the selected fragmented peptide ions from the first set of fragmented peptide ions correspond with the selected fragmented peptide ions from the second set of fragmented peptide ions. In certain embodiments, the selected fragmented peptide ions from the first set of fragmented peptide ions are b ions and the selected fragmented peptide ions from the second set of fragmented peptide ions are b ions having a difference in mass of an arginine amino acid residue or a mass of a lysine amino acid residue. In certain embodiments, the selected fragmented peptide ions from the first set of fragmented peptide ions are y ions and the selected fragmented peptide ions from the second set of fragmented peptide ions are y ions having a difference in mass of an arginine amino acid residue or a mass of a lysine amino acid residue.

In some examples, the samples are subjected to sample pre-processing, for example to purify biomolecules of interest, for example for mass spectral analysis. In some examples, sample preprocessing comprises one or more of gel electrophoresis, liquid chromatography, gas chromatography, capillary electrophoresis, capillary gel electrophoresis, isoelectric focusing chromatography, paper chromatography, thin-layer chromatography; nano-flow chromatography, micro-flow chromatography, high-flow-rate chromatography, reversed-phase chromatography, normal-phase chromatography, hydrophilic-interaction chromatography, ion exchange chromatography, porous graphitic chromatography, size-exclusion chromatography, affinity-based, chromatography, chip-based microfluidics, high-performance liquid chromatography, ultra-high-pressure liquid chromatography or flow-pressure liquid chromatography. In some embodiments, the sample is subjected to sample pre-processing to remove any post translational modifications, such as glycosylation, that might complicate the determination of the mass of a peptide and/or peptide ion.

It is envisioned that certain aspects and/or steps of the method disclosed herein can be performed on one or more computing machines, which may be part of a mass spectrometer or separate from a mass spectrometer.

Figure 13:
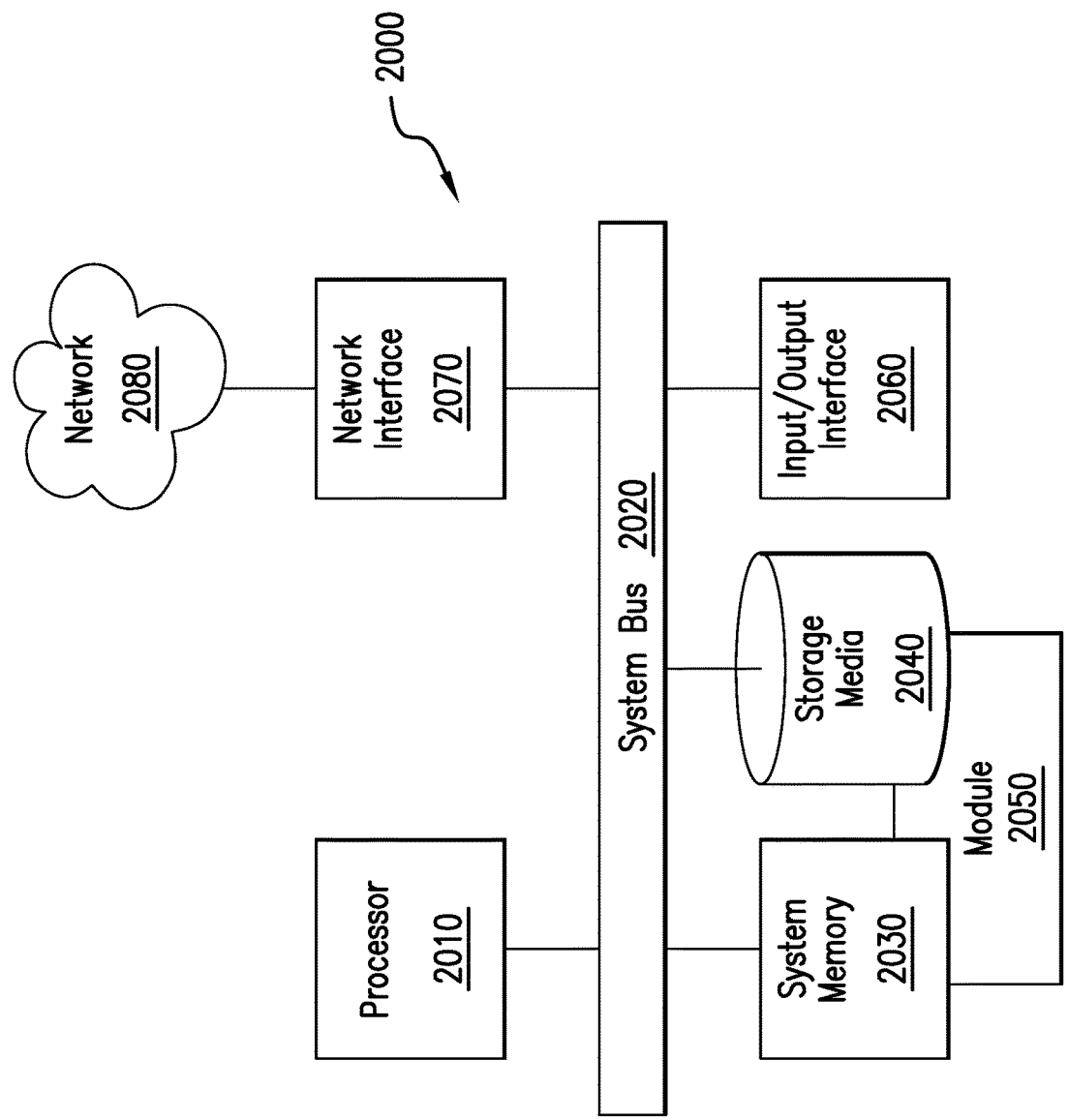
FIG. 13 is an exemplary computing system that may be used to carry out various steps of a method of de novo polypeptide sequencing, in accordance with certain exemplary embodiments.

FIG. 13 depicts a computing machine 2000 and a module 2050 in accordance with certain exemplary embodiments, for the determination of the amino acid sequence of a polypeptide, such as a monoclonal antibody or other protein. The computing machine 2000 may correspond to any of various computers, servers, mobile devices, embedded systems, or computing systems. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080. In some examples, the computing machine may be part of a mass spectrometer, connected to a mass spectrometer, and/or capable of receiving data from a mass spectrometer, such as through a network, for example receiving mass spectra data corresponding to the b and y fragment ions produced in a tandem mass spectrometer.

The computing machine 2000 may be implemented as a conventional computer system, an embedded controller, a laptop, a server, a mobile device, a smartphone, one more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations as functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain example embodiments, the processor 2010 along with other components of the computing machine 2000 may be a virtualized computing machine executing within one or more other computing machines.

The system memory 2030 may include non-volatile memories such as read only memory ("ROM"), programmable read-only memory ("PROM"), erasable programmable read-only memory ("EPROM"), flash memory, or any other device capable of storing program instructions or data with or without applied power. The system memory 2030 may also include volatile memories such as random access memory ("RAM"), static random access memory ("SRAM"), dynamic random access memory ("DRAM"), and synchronous dynamic random access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device such as the storage media 2040.

The storage media 2040 may include a hard disk, a floppy disk, a compact disc read only memory ("CD-ROM"), a digital versatile disc ("DVD"), a Blu-ray disc, a magnetic tape, a flash memory, other non-volatile memory device, a solid state drive ("SSD"), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for operably coupling the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attached ("ATA"), serial ATA ("SAT A"), universal serial bus ("USB"), Thunderbolt, Fire Wire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks (WAN), local area networks (LAN), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or an analog communication media such as fiber optic cables, free-space optics, waveguides, electrical conductors, wireless links, antennas, radio-frequency communications, and so forth.

The processor 2010 may be connected to the other elements of the computing machine 2000 or the various peripherals through the system bus 2020. It should be appreciated that the system bus 2020 may be within the processor 2010, outside the processor 2010, or both. According to some embodiments, any of the processor 2010, the other elements of the computing machine 2000, or the various peripherals discussed herein may be integrated into a single device such as a system on chip ("SOC"), system on package ("SOP"), or ASIC device.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement an embodiment of the disclosed embodiments based on the appended flow chart and/or associated description in the application text. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described previously. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of various embodiments. Accordingly, such alternative embodiments are included in the examples described herein.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

The following examples are provided to illustrate particular features of certain embodiments. However, the particular features described below should not be considered as limitations on the scope of the invention, but rather as examples from which equivalents will be recognized by those of ordinary skill in the art.

Example

The following example is put forth so as to provide those of ordinary skill in the art with a complete disclosure and description of how to make and use the methods of the invention, and is not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight unless indicated, temperature is in degrees Centigrade, room temperature is about 25° C., and pressure is at or near atmospheric.

Two samples containing Bovine Serum Albumin (BSA) were subjected to digestion by Trypsin and Tryp-N, (a thermophilic metalloprotease with N-terminal specificity for arginine and lysine developed at Cold Spring Harbor laboratory and commercially available from Protifi, LLC) respectfully. The resulting peptide digests were individually subjected to Tandem Mass Spectrometry to determine the amino acid sequence of digested peptide fragments of the BSA. FIG. 1 shows the bovine serum albumin (BSA) sequence coverage using a Tryp-N protease digestion. The sequence coverage is 91.4%. Various peptide fragments generated from a Tryp-N digest are shown below the BSA protein sequence (SEQ ID NO: 1). FIG. 2 shows the BSA sequence coverage using a Trypsin protease digestion. The sequence coverage is 94.2%. Various peptide fragments generated from the Trypsin digest are shown below the BSA protein sequence (SEQ ID NO: 1).

To determine the sequence of the peptides in each of the digested samples, individual peptides were selected from the quadupole and subjected to collisionally induced fragmentation to produce b and y peptide fragment ions (see, for example, FIGS. 5A, 5B, 7A, 7B, 9A, 9B, 11A and 11B).

Figure 4:
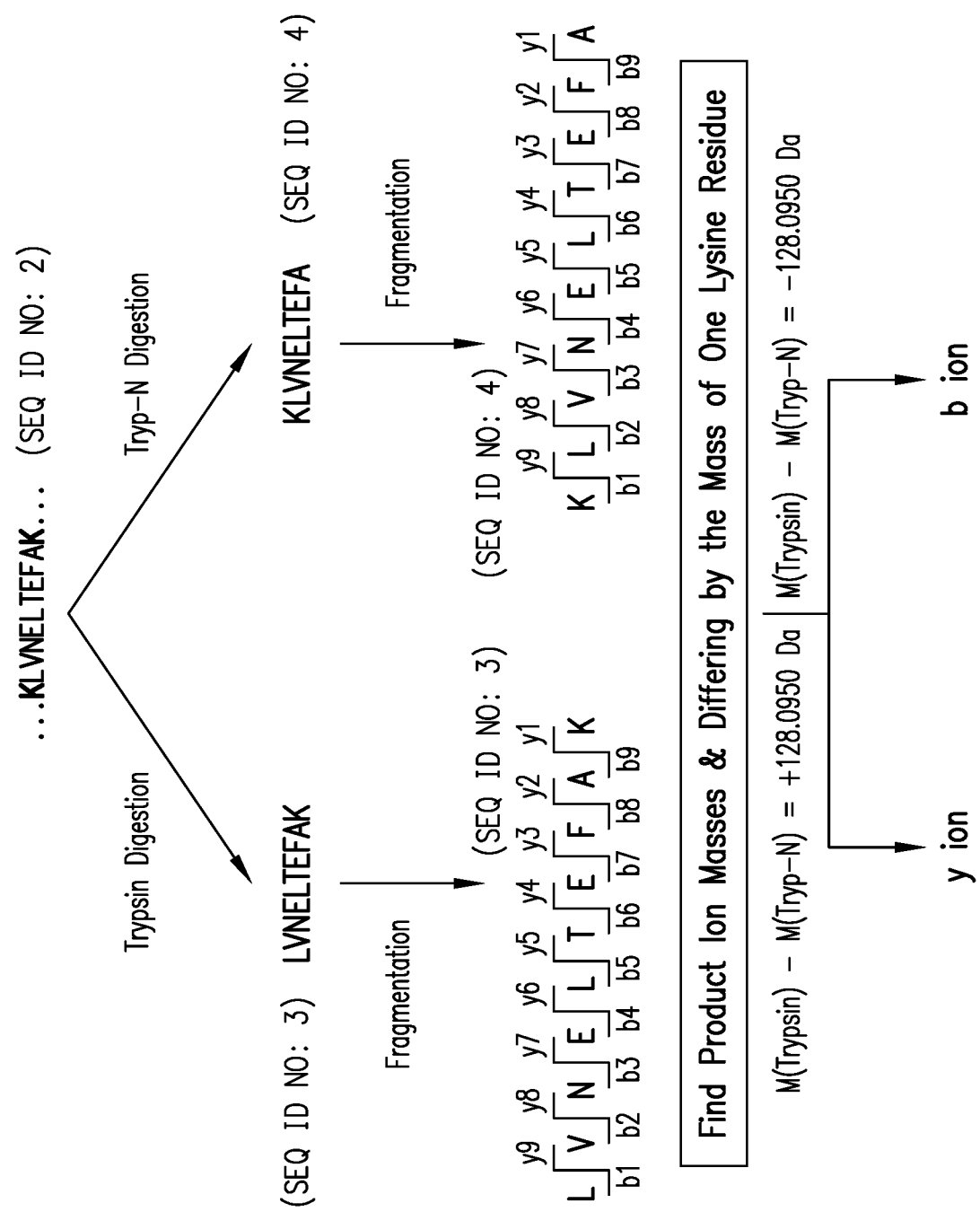
FIG. 4 shows the analysis of a peptide from BSA generated as described in case (1) from FIG. 3. For a polypeptide including the sequence KLVNELTEFAK (SEQ ID NO: 2) digestion with Trypsin yields the peptide LVNELTEFAK (SEQ ID NO: 3). Digestion with Tryp-N yields the peptide KLVNELTEFA (SEQ ID NO: 4). The two peptides have the same mass. However, when fragmented during Mass Spec Analysis, resulting b ions from each peptide or y ions from each peptide differ by the mass of a single lysine amino acid residue.
Figure 5A:
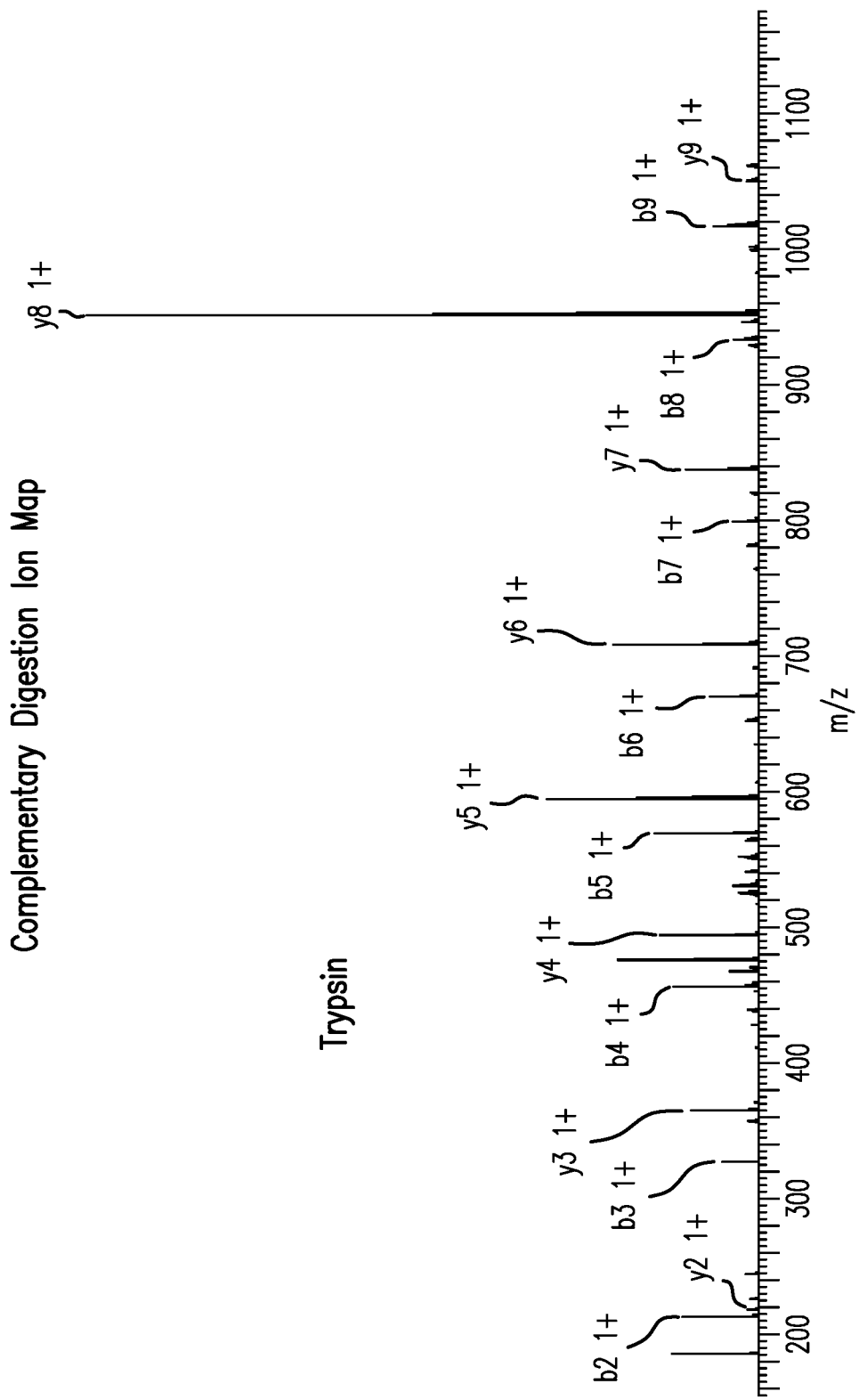
FIGS. 5A-5C show the resulting mass spectra from the analysis shown in FIG. 4 for the Trypsin digest and the Tryp-N digest, and the generation of the primary sequence of the peptide from Trypsin and Tryp-N ion maps generated from the mass spectra.
Figure 5B:
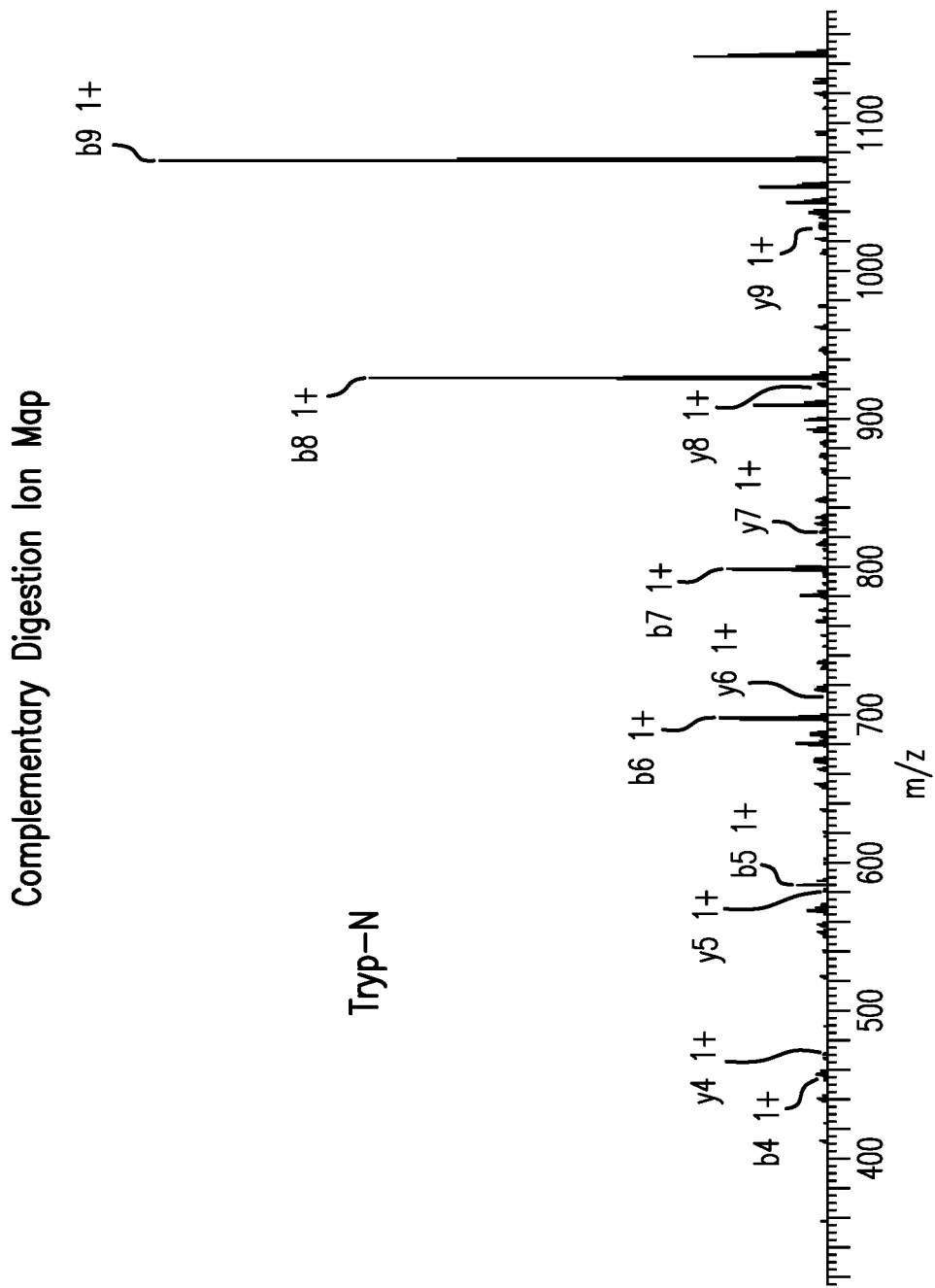
Figure 5C:
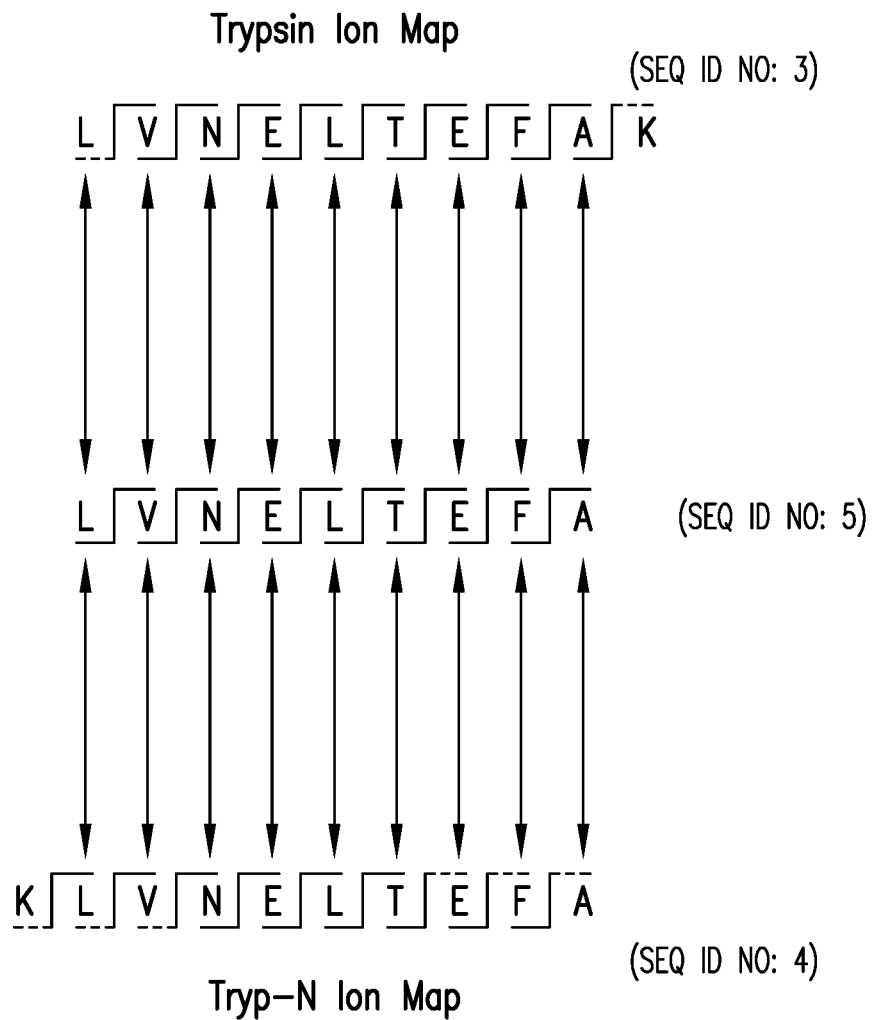
Figure 6:
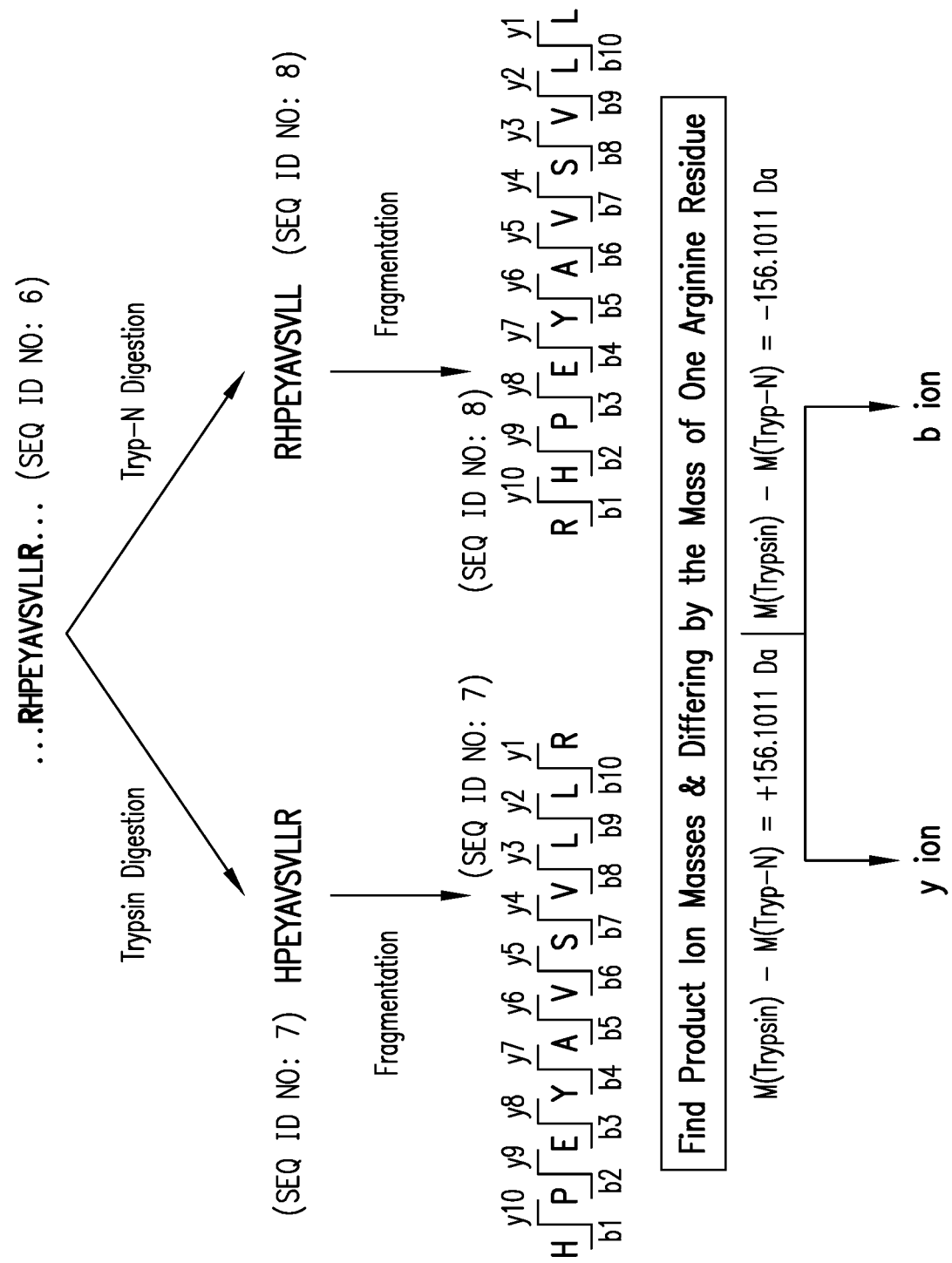
FIG. 6 shows the analysis of a peptide from BSA generated as described in case (2) from FIG. 3. For a polypeptide including the sequence RHPEYAVSVLLR (SEQ ID NO: 6) digestion with Trypsin yields the peptide HPEYAVSVLLR (SEQ ID NO: 7). Digestion with Tryp-N yields the peptide RHPEYAVSVLL (SEQ ID NO: 8). The two peptides have the same mass. However, when fragmented during mass spec analysis, resulting b ions from each peptide or y ions from each peptide differ by the mass of a single arginine amino acid residue.
Figure 7A:
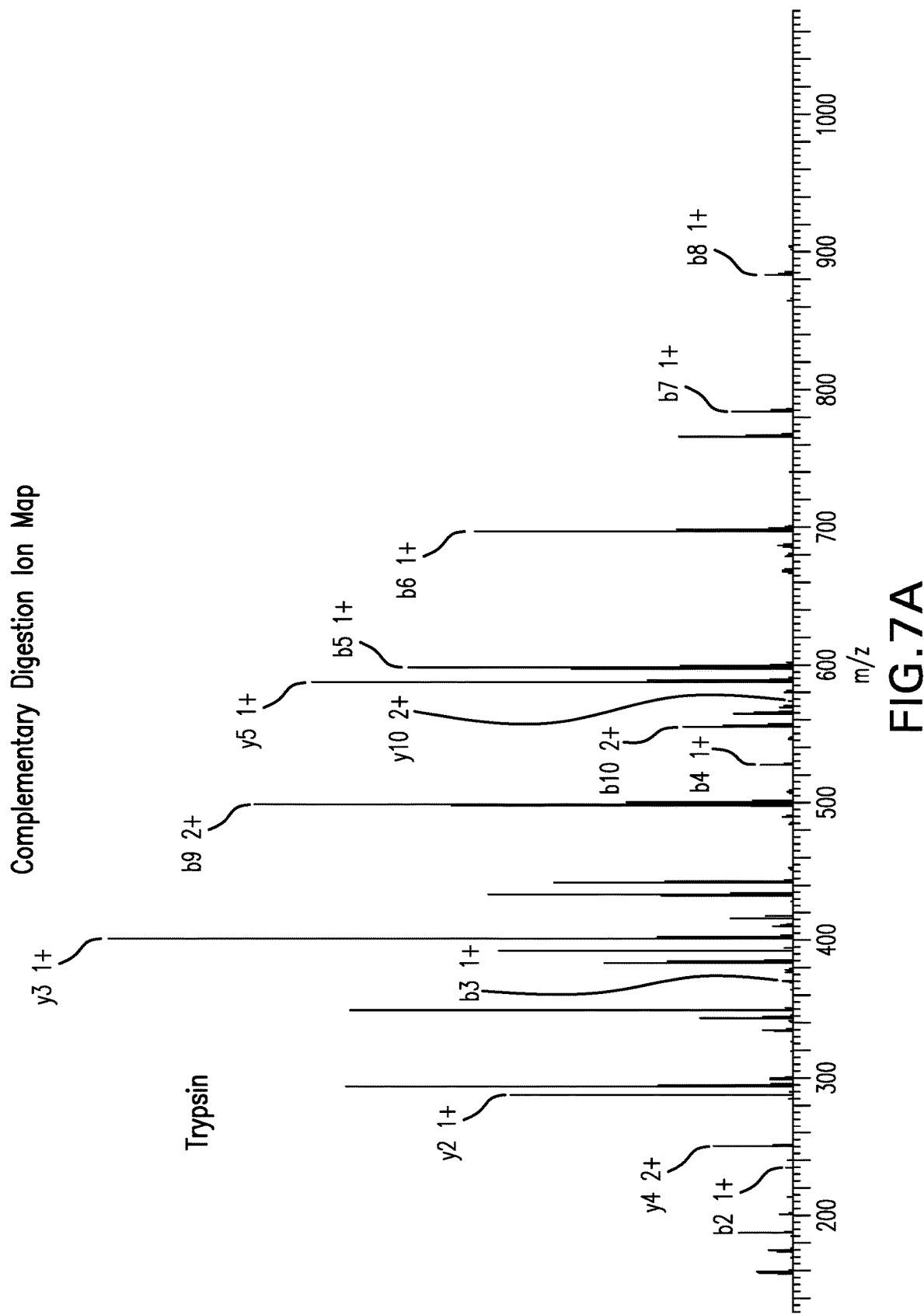
FIGS. 7A-7C show the resulting mass spectra from the analysis shown in FIG. 6 for the Trypsin digest and the Tryp-N digest, and the generation of the primary sequence of the peptide from the Trypsin and Tryp-N ion maps generated from the mass spectra.
Figure 7B:
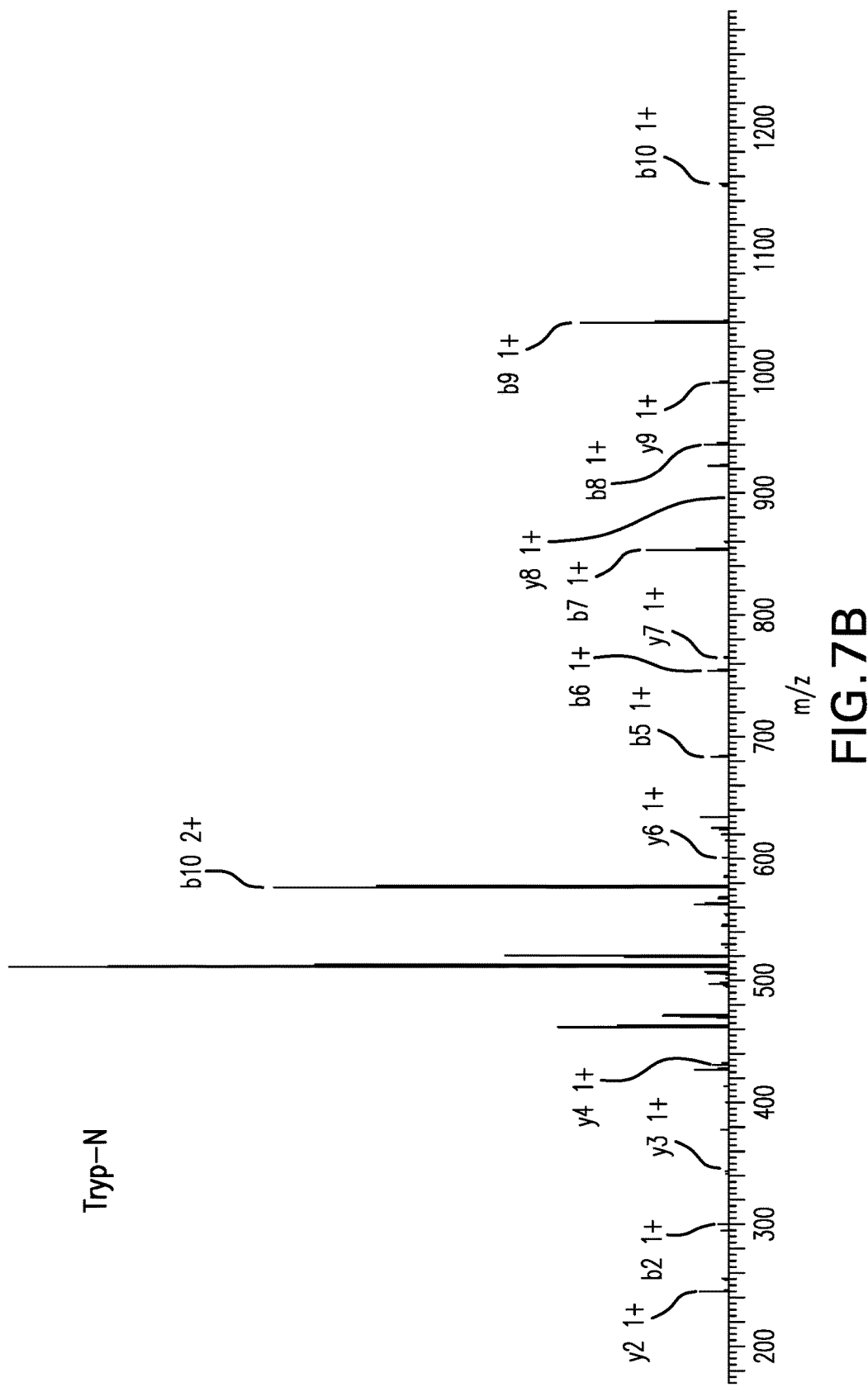
Figure 7C:
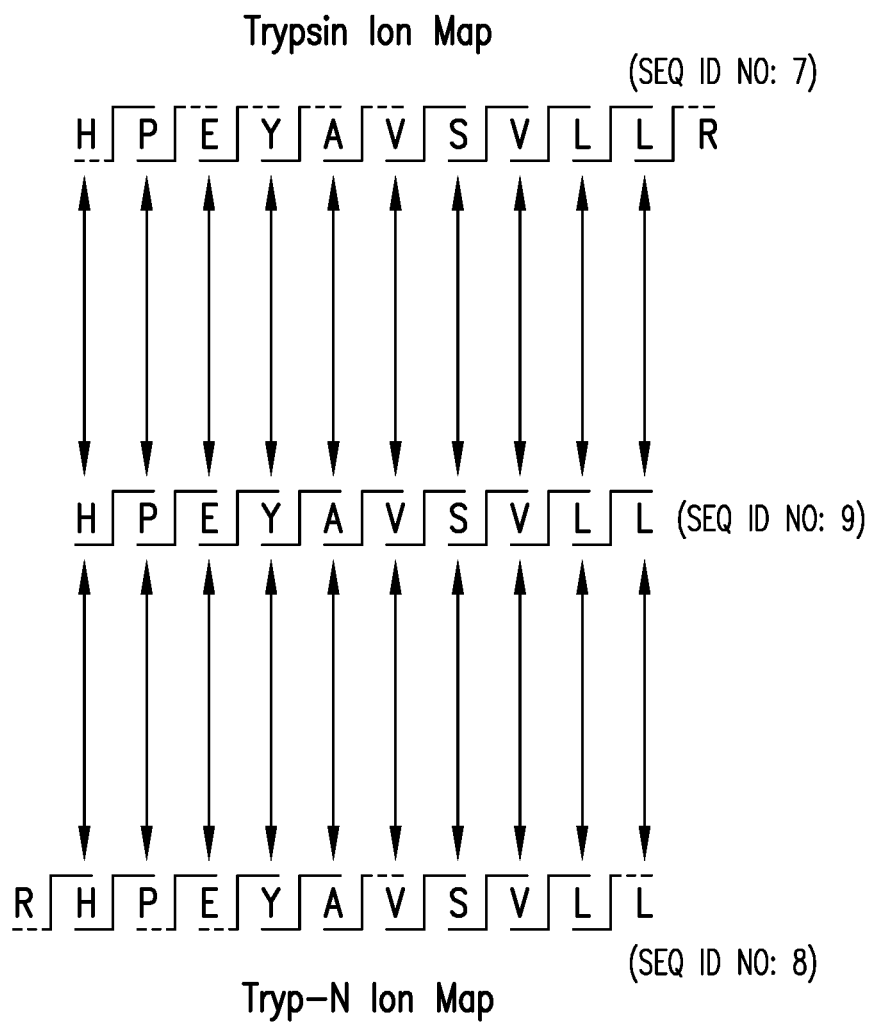
Figure 8:
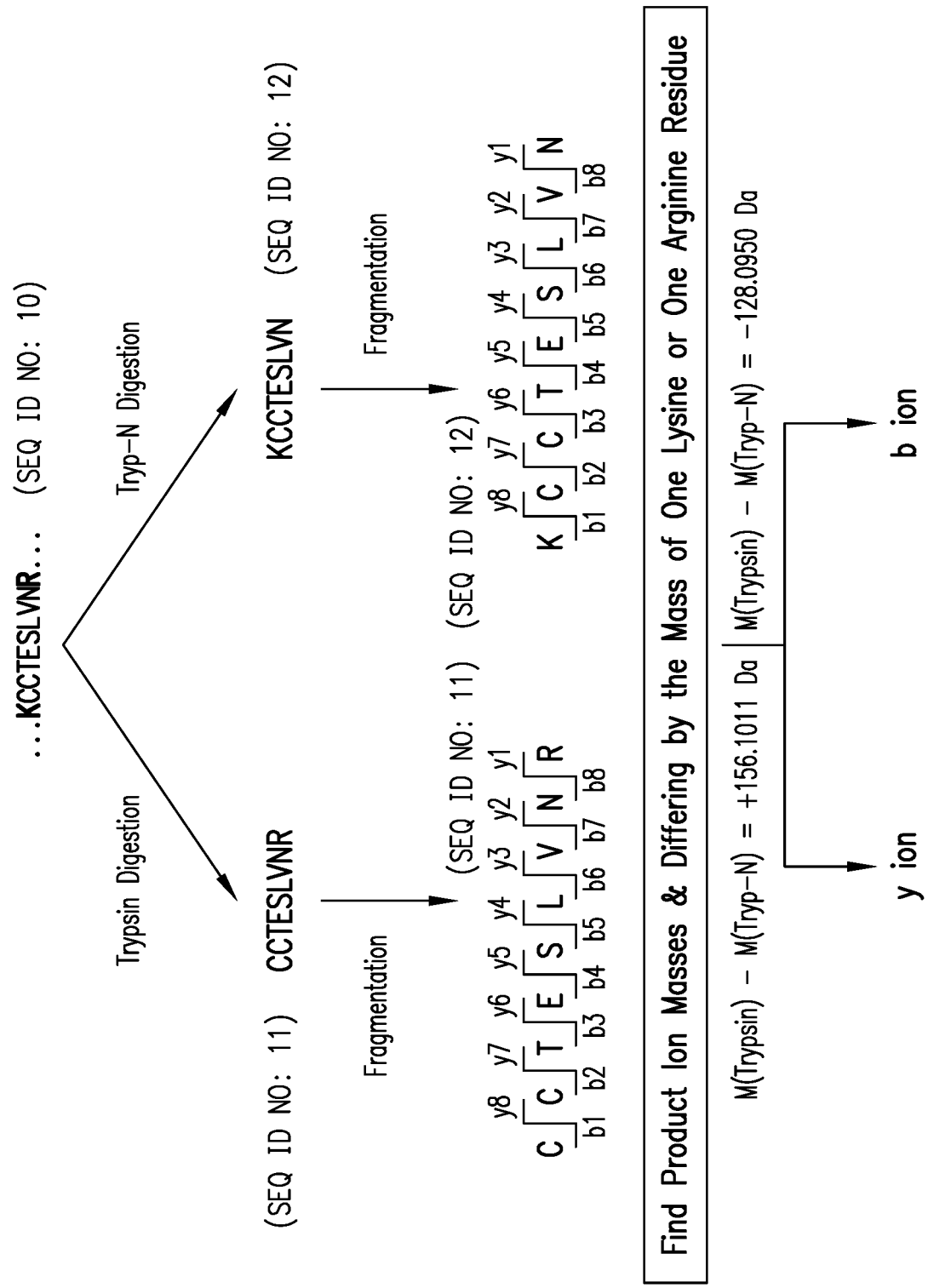
FIG. 8 shows the analysis of a peptide from BSA generated as described in case (3) from FIG. 3. For a polypeptide including the sequence KCCTESLVNR (SEQ ID NO: 10) digestion with Trypsin yields the peptide CCTESLVNR (SEQ ID NO: 11). Digestion with Tryp-N yields the peptide KCCTESLVN (SEQ ID NO: 12). In this case the two peptides do not have the same mass. However, when fragmented during Mass Spec Analysis, the resulting b ions from each peptide or y ions from each peptide differ by the mass of a single lysine amino acid residue (b ions) or a single arginine amino acid residue (y ions).
Figure 9A:
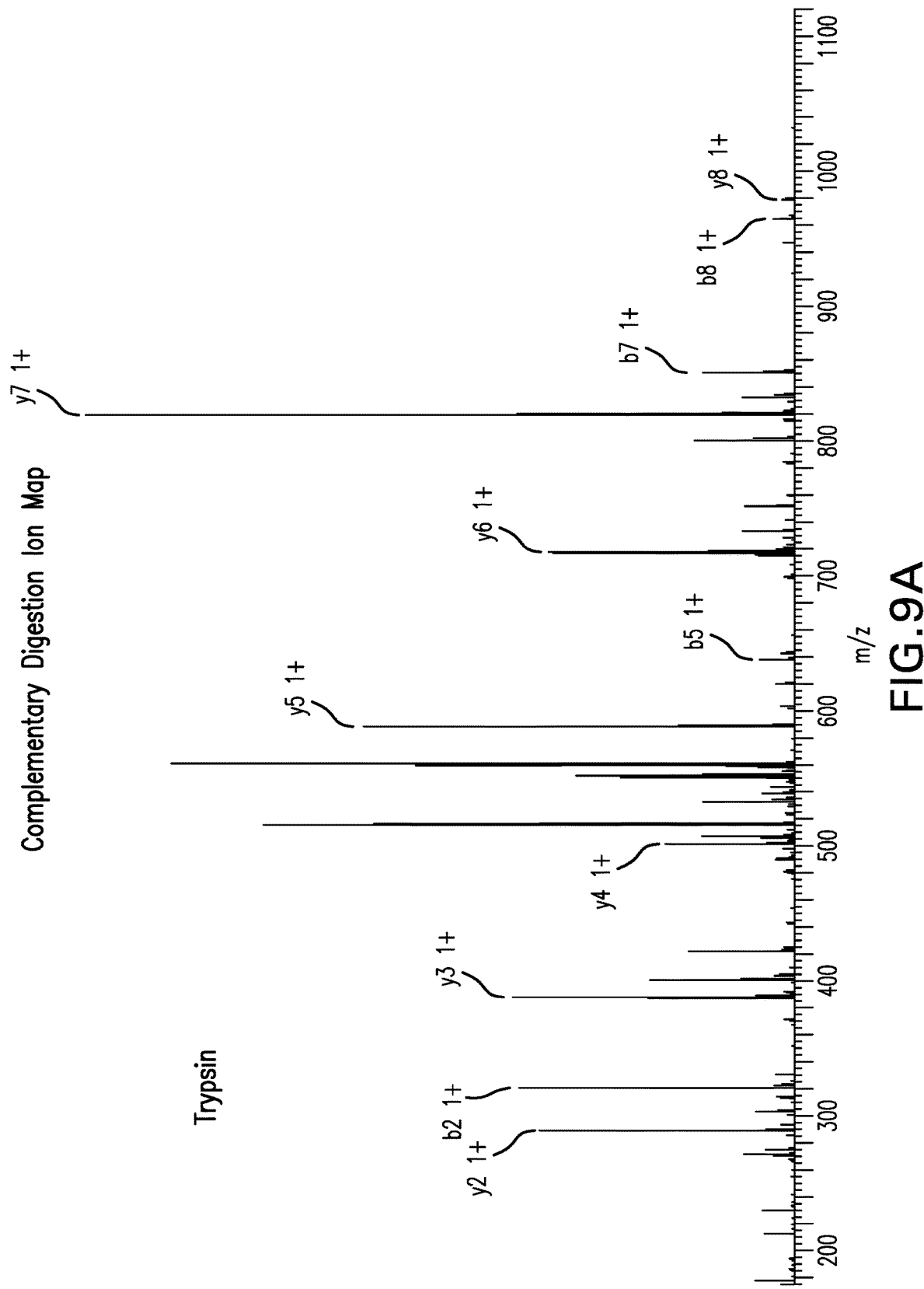
FIGS. 9A-9C show the resulting mass spectra from the analysis shown in FIG. 8 for the Trypsin digest and the Tryp-N digest and the generation of the primary sequence of the peptide from the Trypsin and Tryp-N ion maps generated from the mass spectra.
Figure 9B:
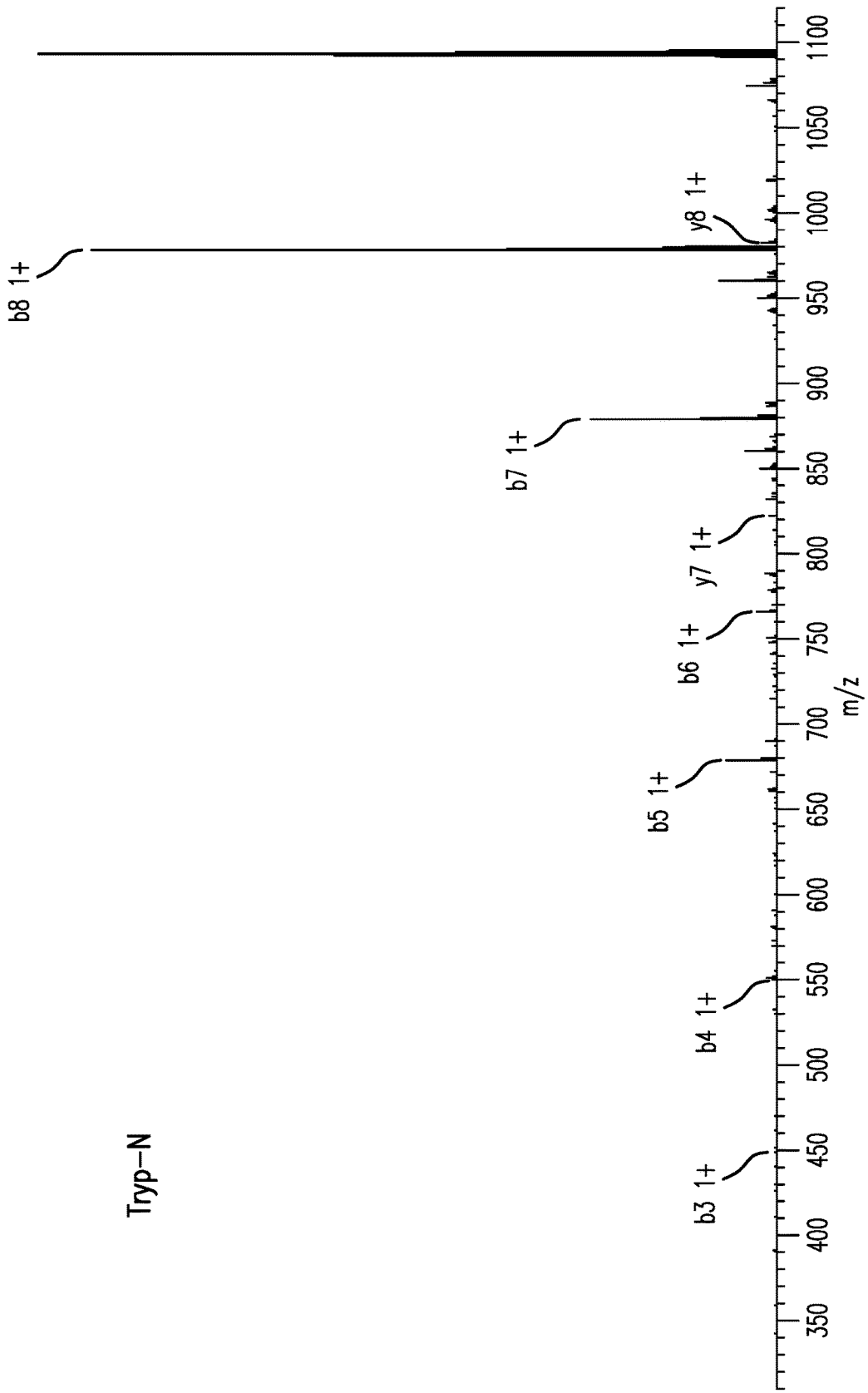
Figure 9C:
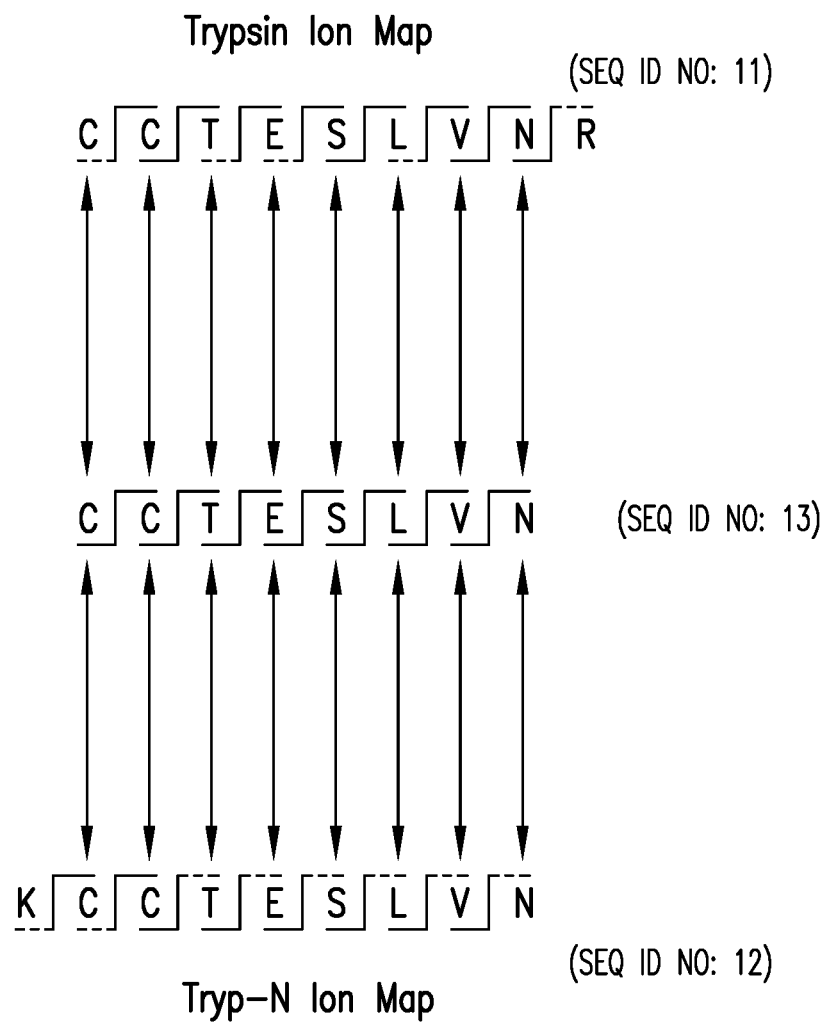
Figure 10:
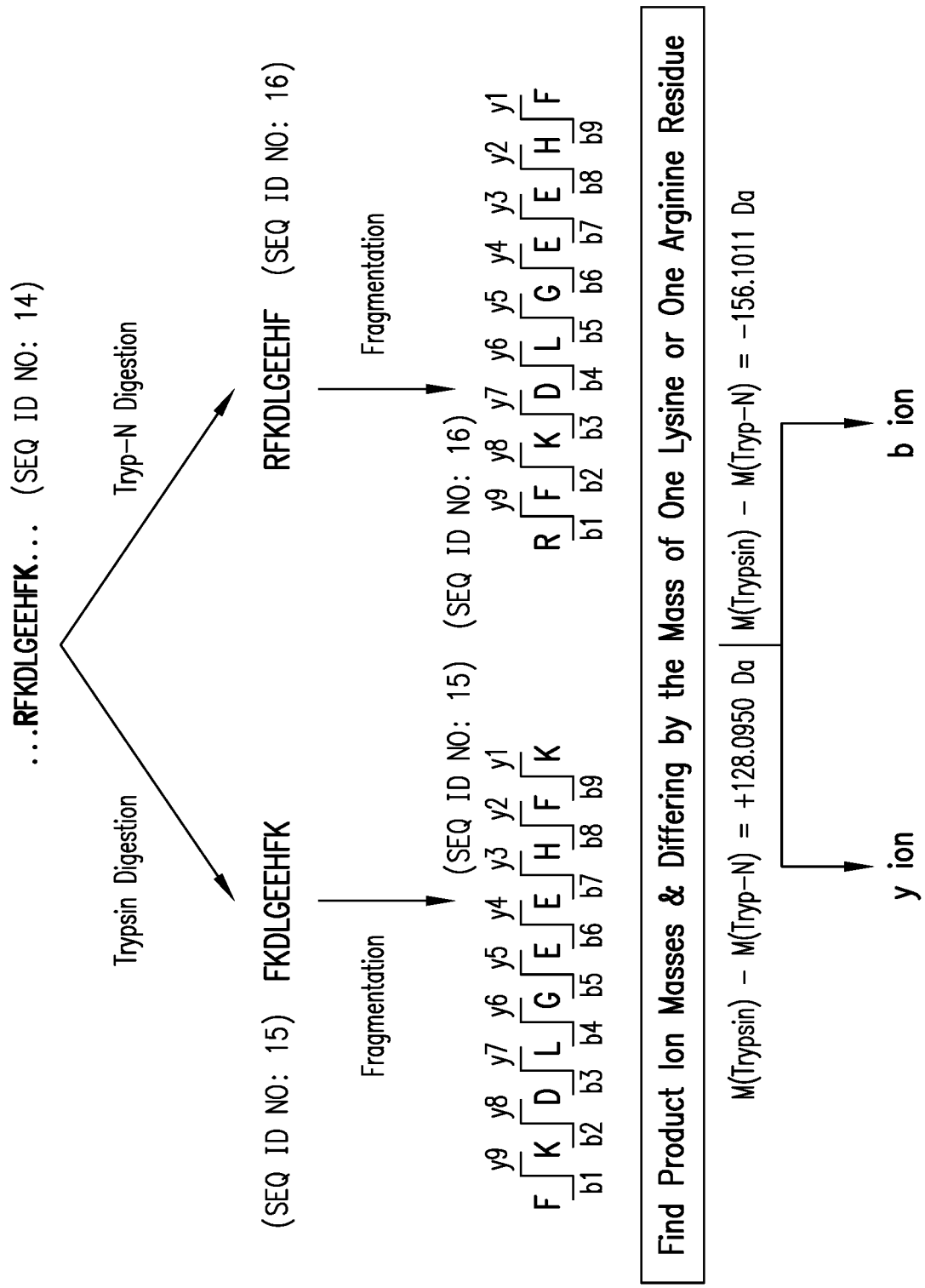
FIG. 10 shows the analysis of a peptide from BSA generated as described in case (4) from FIG. 3. For a polypeptide including the sequence RFKDLGEEHFK (SEQ ID NO: 14) digestion with Trypsin yields the peptide FKDLGEEHFK (SEQ ID NO: 15). Digestion with Tryp-N yields the peptide RFKDLGEEHF (SEQ ID NO: 16). In this case the two peptides do not have the same mass. However, when fragmented during mass spec analysis, the resulting b ions from each peptide or y ions from each peptide differ in mass by a single lysine amino acid residue (y ions) or a single arginine amino acid residue (b ions).
Figure 11A:
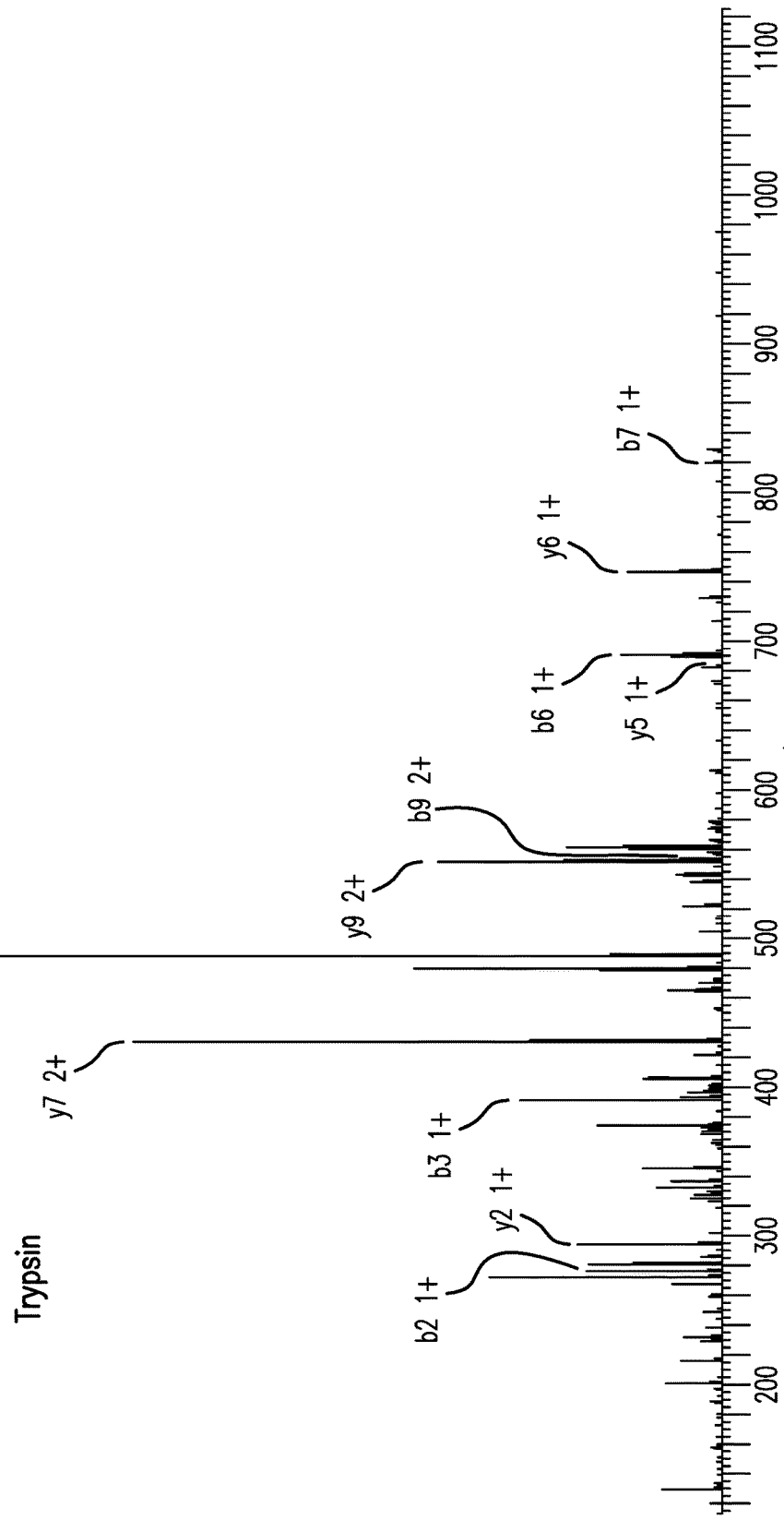
FIGS. 11A-11C show the resulting Mass Spectra from the analysis shown in FIG. 10 for the Trypsin digest and the Tryp-N digest, and the generation of the primary sequence of the peptide from the Trypsin and Tryp-N ion maps generated from the mass spectra.
Figure 11B:
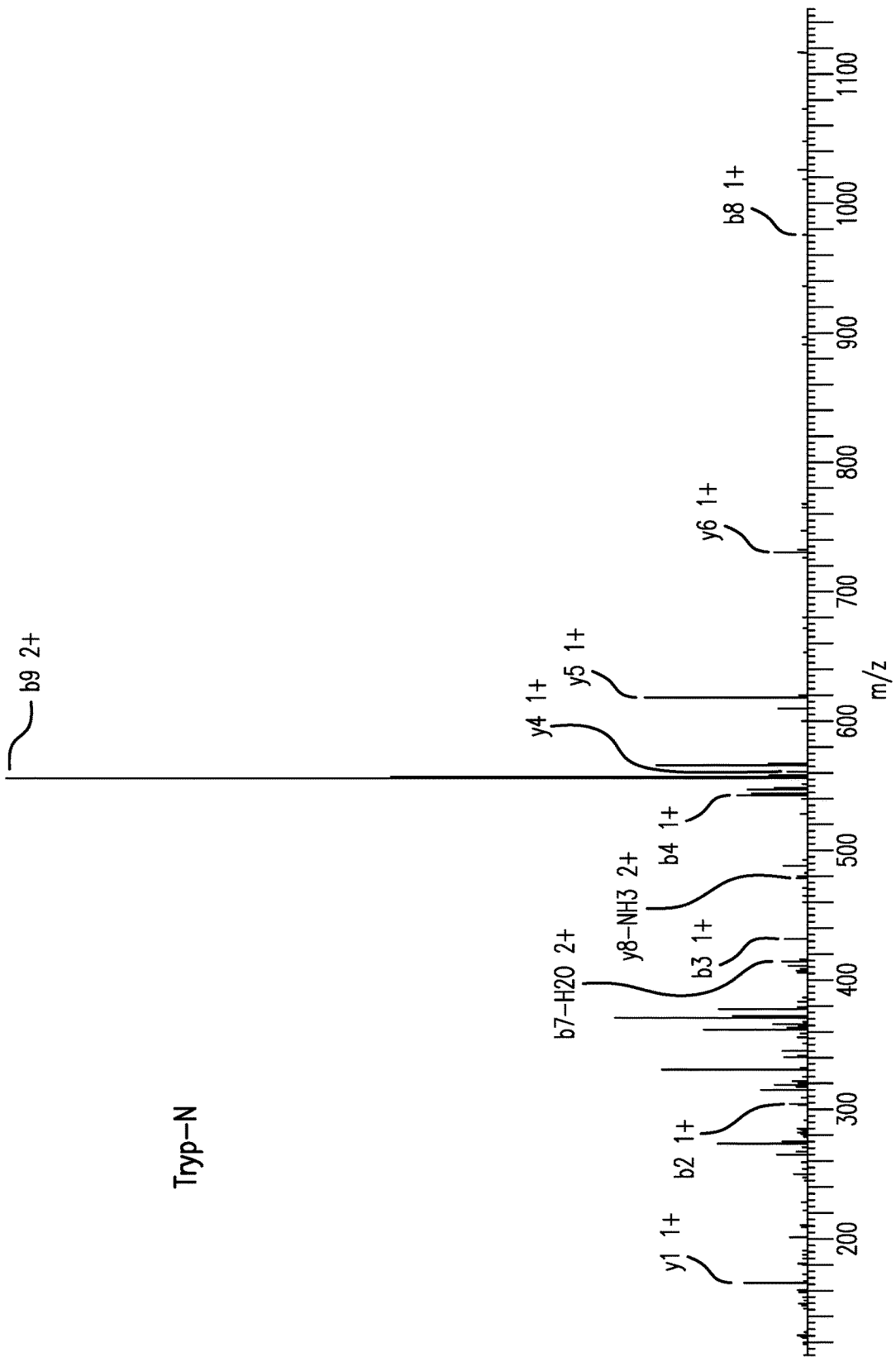
Figure 11C:
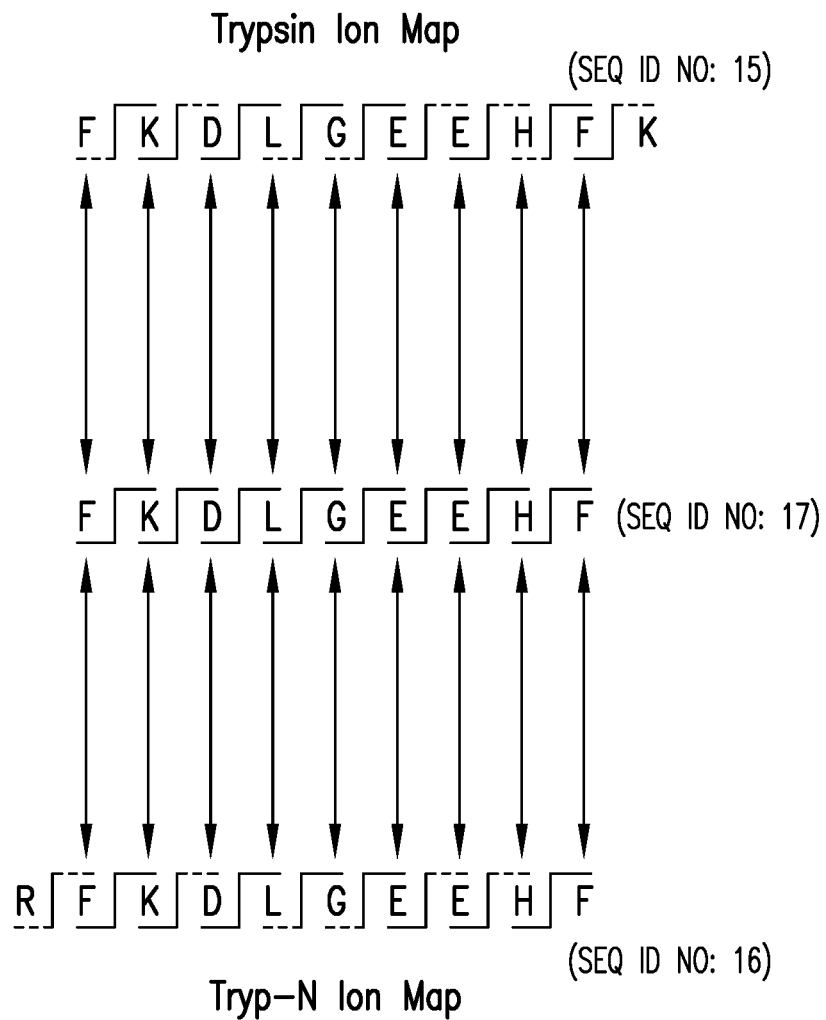

The individual ion maps were then used to determine the primary sequences of the individual peptides as shown in FIGS. 5C, 7C, 9C, and 11C, following the procedure shown in FIGS. 4, 6, 8, and 10, respectively. Briefly, as shown in FIG. 4 for a polypeptide including the sequence KLVNELTEFAK (SEQ ID NO: 2) digestion with Trypsin yielded the peptide LVNELTEFAK (SEQ ID NO: 3). Digestion with Tryp-N yields the peptide KLVNELTEFA (SEQ ID NO: 4). The two peptides have the same mass. However, when fragmented during mass spec analysis, the b ions and the y ions from the Trypsin digest differed in mass by a single lysine residue from the b ions and y ions from the Tryp-N digest. Similarly as shown in FIG. 6, a polypeptide including the sequence RHPEYAVSVLLR (SEQ ID NO: 6) yielded the peptide HPEYAVSVLLR (SEQ ID NO: 7) when digested with Trypsin. Digestion with Tryp-N yielded the peptide RHPEYAVSVLL (SEQ ID NO: 8). The two peptides have the same mass. However, when fragmented during mass spec analysis, the b ions and the y ions from the Trypsin digest differed in mass by a single arginine residue from the b ions and y ions from the Tryp-N digest. A slightly different situation was observed for peptides bounded by a mixture of arginine and lysine residues. As shown in FIG. 8, for a polypeptide including the sequence KCCTESLVNR (SEQ ID NO: 10), digestion with Trypsin yielded the peptide CCTESLVNR (SEQ ID NO: 11). Digestion with Tryp-N yielded the peptide KCCTESLVN (SEQ ID NO: 12). In this case the two peptides do not have the same mass. However, when fragmented during mass spec analysis, the resulting b ions from each peptide or y ions from each peptide differ by the mass of a single lysine amino acid residue (b ions) or a single arginine amino acid residue (y ions). FIG. 10 shows that for a polypeptide including the sequence RFKDLGEEHFK (SEQ ID NO: 14), digestion with Trypsin yielded the peptide FKDLGEEHFK (SEQ ID NO: 15). Digestion with Tryp-N yielded the peptide RFKDLGEEHF (SEQ ID NO: 16). In this case the two peptides do not have the same mass. However, when fragmented during mass spec analysis, the resulting b ions from each peptide or y ions from each peptide differ in mass by a single lysine amino acid residue (y ions) or a single arginine amino acid residue (b ions).

Once the b and y ion types are determined, a list of the same-type peptide ions is generated in each set of fragment peptide ions and a mass ladder of peptide ions with incremental mass by the mass of amino acid residue(s) is generated from the list. The mass differences between two adjacent peptide ions in the mass ladder were assigned to specific amino acid residue(s) based on the mass of the individual 20 amino acids. Using a set of b and y ions for a peptide, such as shown in SEQ ID NOS: 2, 6, 10, and 14, from both the Trypsin digest and the Tryp-N digest, individual amino acid residues identified from them were used to assemble a primary sequence for the peptide from which they were derived. The individual peptides were then used to assemble the primary sequence of BSA.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for determining an amino acid sequence of a polypeptide of interest, comprising:

contacting a first sample containing the polypeptide of interest with Trypsin protease, under conditions that permit the Trypsin protease to digest the polypeptide of interest to produce a first set of digested peptide fragments;

fragmenting the first set of digested peptide fragments with a mass spectrometer to produce a first set of fragmented peptide ions corresponding to peptides in the first set of digested peptide fragments;

determining masses of the first set of fragmented peptide ions;

contacting a second sample containing the polypeptide of interest with Tryp-N protease, under conditions that permit the Tryp-N protease to digest the polypeptide of interest to produce a second set of digested peptide fragments;

fragmenting the second set of digested peptide fragments with a mass spectrometer to produce a second set of fragmented peptide ions corresponding to peptides in the second set of digested peptide fragments;

determining masses of the second set of fragmented peptide ions;

selecting pairs of peptide ions from the first set of fragmented peptide ions and the second set of fragmented peptide ions that differ in mass by a mass of an arginine amino acid residue or a mass of a lysine amino acid residue;

assigning ion type for the pairs of peptide ions to generate a list of the same-type peptide ions;

selecting a mass ladder of peptide ions with incremental mass by the mass of amino acid residue(s) to identify individual amino acid residues and assembling the identified amino acid residues to determine the amino acid sequence of the polypeptide of interest.

2. The method of claim 1, further comprising, selecting a first digested peptide fragment from the first set of digested peptide fragments; and selecting a second digested peptide fragment from the second set of digested peptide fragments with a mass identical to the first digested peptide fragment.

3. The method of claim 1, wherein the first digested peptide fragment from the first set of digested peptide fragments is fragmented to produce a first series of fragmented peptide ions corresponding to the first digested peptide fragment and the second digested peptide fragment from the second set of digested peptide fragments corresponding to the first digested peptide fragment is fragmented to produce a second series of fragmented peptide ions corresponding to the second digested peptide fragment; and wherein assigning the pairs of peptide ions to derive amino acid sequences comprises:

assigning ion type for the pairs of peptide ions to generate a list of the same-type peptide ions;

selecting a mass ladder of peptide ions with incremental mass by the mass of amino acid residue(s) to identify individual amino acid residues for the list; and assembling the identified amino acid residues to determine the amino acid sequence of the polypeptide of interest.

4. The method of claim 3, wherein the pairs of peptide ions from the first set of fragmented peptide ions and the second set of fragmented peptide ions are selected that differ in mass by the mass of an arginine amino acid residue.

5. The method of claim 4, where a negative difference in mass of an arginine amino acid residue between pairs of peptide ions from the first set of fragmented peptide ions and the second set of fragmented peptide ions indicates that the peptide has an N-terminal arginine residue.

6. The method of claim 4, where a positive difference in mass of an arginine amino acid residue between pairs of peptide ions from the first set of fragmented peptide ions and the second set of fragmented peptide ions indicates that the peptide has a C-terminal arginine residue.

7. The method of claim 1, wherein the pairs of peptide ions from the first set of fragmented peptide ions and the second set of fragmented peptide ions are selected that differ in mass by the mass of a lysine amino acid residue.

8. The method of claim 7, where a negative difference in mass of a lysine amino acid residue between pairs of peptide ions from the first set of fragmented peptide ions and the second set of fragmented peptide ions indicates that the peptide has an N-terminal lysine residue.

9. The method of claim 7, where a positive difference in mass of a lysine amino acid residue between pairs of peptide ions from the first set of fragmented peptide ions and the second set of fragmented peptide ions indicates that the peptide has a C-terminal lysine residue.

10. The method of claim 9, wherein the selected fragmented peptide ions from the first set of fragmented peptide ions correspond with the selected fragmented peptide ions from the second set of fragmented peptide ions.

11. The method of claim 10, wherein the selected fragmented peptide ions from the first set of fragmented peptide ions are b ions and the selected fragmented peptide ions from the second set of fragmented peptide ions are b ions having a difference in mass of an arginine amino acid residue or a mass of a lysine amino acid residue.

12. The method of claim 10, wherein the selected fragmented peptide ions from the first set of fragmented peptide ions are y ions and the selected fragmented peptide ions from the second set of fragmented peptide ions are y ions having a difference in mass of an arginine amino acid residue or a mass of a lysine amino acid residue.

13. The method of claim 12, wherein mass is determined using mass spectrometry.

14. The method of claim 13, wherein the fragment ions are produced using tandem mass spectrometry.

15. The method of claim 14, wherein the polypeptide of interest comprises a protein.

16. The method of claim 15, wherein the polypeptide of interest comprises a monoclonal antibody.

17. The method of claim 16, wherein the polypeptide of interest comprises a monospecific antibody or a bispecific antibody.

18. The method of claim 1, wherein the pairs of peptide ions from the first set of fragmented peptide ions and the second set of fragmented peptide ions that are selected, differ in mass by a mass of an arginine amino acid residue and a mass of a lysine amino acid residue.

19. The method of claim 1, wherein the first sample and the second sample are preprocessed.

* * * * *

SEQUENCE LISTING

```
<160> NUMBER OF SEQ ID NOS: 17

<210> SEQ ID NO 1
<211> LENGTH: 583
<212> TYPE: PRT
<213> ORGANISM: Bos taurus

<400> SEQUENCE: 1

Asp Thr His Lys Ser Glu Ile Ala His Arg Phe Lys Asp Leu Gly Glu
1               5                   10                  15

Glu His Phe Lys Gly Leu Val Leu Ile Ala Phe Ser Gln Tyr Leu Gln
                20                  25                  30

Gln Cys Pro Phe Asp Glu His Val Lys Leu Val Asn Glu Leu Thr Glu
            35                  40                  45

Phe Ala Lys Thr Cys Val Ala Asp Glu Ser His Ala Gly Cys Glu Lys
    50                  55                  60

Ser Leu His Thr Leu Phe Gly Asp Glu Leu Cys Lys Val Ala Ser Leu
65                  70                  75                  80

Arg Glu Thr Tyr Gly Asp Met Ala Asp Cys Cys Glu Lys Gln Glu Pro
                85                  90                  95

Glu Arg Asn Glu Cys Phe Leu Ser His Lys Asp Asp Ser Pro Asp Leu
            100                 105                 110

Pro Lys Leu Lys Pro Asp Pro Asn Thr Leu Cys Asp Glu Phe Lys Ala
        115                 120                 125

Asp Glu Lys Lys Phe Trp Gly Lys Tyr Leu Tyr Glu Ile Ala Arg Arg
    130                 135                 140

His Pro Tyr Phe Tyr Ala Pro Glu Leu Leu Tyr Tyr Ala Asn Lys Tyr
145                 150                 155                 160

Asn Gly Val Phe Gln Glu Cys Cys Gln Ala Glu Asp Lys Gly Ala Cys
                165                 170                 175

Leu Leu Pro Lys Ile Glu Thr Met Arg Glu Lys Val Leu Thr Ser Ser
            180                 185                 190

Ala Arg Gln Arg Leu Arg Cys Ala Ser Ile Gln Lys Phe Gly Glu Arg
        195                 200                 205

Ala Leu Lys Ala Trp Ser Val Ala Arg Leu Ser Gln Lys Phe Pro Lys
    210                 215                 220

Ala Glu Phe Val Glu Val Thr Lys Leu Val Thr Asp Leu Thr Lys Val
225                 230                 235                 240

His Lys Glu Cys Cys His Gly Asp Leu Leu Glu Cys Ala Asp Asp Arg
                245                 250                 255

Ala Asp Leu Ala Lys Tyr Ile Cys Asp Asn Gln Asp Thr Ile Ser Ser
            260                 265                 270
```

-continued

```
Lys Leu Lys Glu Cys Cys Asp Lys Pro Leu Leu Glu Lys Ser His Cys
            275                 280                 285

Ile Ala Glu Val Glu Lys Asp Ala Ile Pro Glu Asn Leu Pro Pro Leu
        290                 295                 300

Thr Ala Asp Phe Ala Glu Asp Lys Asp Val Cys Lys Asn Tyr Gln Glu
305                 310                 315                 320

Ala Lys Asp Ala Phe Leu Gly Ser Phe Leu Tyr Glu Tyr Ser Arg Arg
                325                 330                 335

His Pro Glu Tyr Ala Val Ser Val Leu Leu Arg Leu Ala Lys Glu Tyr
            340                 345                 350

Glu Ala Thr Leu Glu Glu Cys Cys Ala Lys Asp Asp Pro His Ala Cys
        355                 360                 365

Tyr Ser Thr Val Phe Asp Lys Leu Lys His Leu Val Asp Glu Pro Gln
370                 375                 380

Asn Leu Ile Lys Gln Asn Cys Asp Gln Phe Glu Lys Leu Gly Glu Tyr
385                 390                 395                 400

Gly Phe Gln Asn Ala Leu Ile Val Arg Tyr Thr Arg Lys Val Pro Gln
                405                 410                 415

Val Ser Thr Pro Thr Leu Val Glu Val Ser Arg Ser Leu Gly Lys Val
            420                 425                 430

Gly Thr Arg Cys Cys Thr Lys Pro Glu Ser Glu Arg Met Pro Cys Thr
        435                 440                 445

Glu Asp Tyr Leu Ser Leu Ile Leu Asn Arg Leu Cys Val Leu His Glu
450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Ala Leu Thr Pro Asp Glu Thr Tyr
                485                 490                 495

Val Pro Lys Ala Phe Asp Glu Lys Leu Phe Thr Phe His Ala Asp Ile
            500                 505                 510

Cys Thr Leu Pro Asp Thr Glu Lys Gln Ile Lys Lys Gln Thr Ala Leu
        515                 520                 525

Val Glu Leu Leu Lys His Lys Pro Lys Ala Thr Glu Glu Gln Leu Lys
530                 535                 540

Thr Val Met Glu Asn Phe Val Ala Phe Val Asp Lys Cys Cys Ala Ala
545                 550                 555                 560

Asp Asp Lys Glu Ala Cys Phe Ala Val Glu Gly Pro Lys Leu Val Val
                565                 570                 575

Ser Thr Gln Thr Ala Leu Ala
            580

<210> SEQ ID NO 2
<211> LENGTH: 11
<212> TYPE: PRT
<213> ORGANISM: Bos taurus

<400> SEQUENCE: 2

Lys Leu Val Asn Glu Leu Thr Glu Phe Ala Lys
1               5                   10

<210> SEQ ID NO 3
<211> LENGTH: 10
<212> TYPE: PRT
<213> ORGANISM: Bos taurus

<400> SEQUENCE: 3
```

Leu Val Asn Glu Leu Thr Glu Phe Ala Lys
1               5                   10

<210> SEQ ID NO 4
<211> LENGTH: 10
<212> TYPE: PRT
<213> ORGANISM: Bos taurus

<400> SEQUENCE: 4

Lys Leu Val Asn Glu Leu Thr Glu Phe Ala
1               5                   10

<210> SEQ ID NO 5
<211> LENGTH: 9
<212> TYPE: PRT
<213> ORGANISM: Bos taurus

<400> SEQUENCE: 5

Leu Val Asn Glu Leu Thr Glu Phe Ala
1               5

<210> SEQ ID NO 6
<211> LENGTH: 12
<212> TYPE: PRT
<213> ORGANISM: Bos taurus

<400> SEQUENCE: 6

Arg His Pro Glu Tyr Ala Val Ser Val Leu Leu Arg
1               5                   10

<210> SEQ ID NO 7
<211> LENGTH: 11
<212> TYPE: PRT
<213> ORGANISM: Bos taurus

<400> SEQUENCE: 7

His Pro Glu Tyr Ala Val Ser Val Leu Leu Arg
1               5                   10

<210> SEQ ID NO 8
<211> LENGTH: 11
<212> TYPE: PRT
<213> ORGANISM: Bos taurus

<400> SEQUENCE: 8

Arg His Pro Glu Tyr Ala Val Ser Val Leu Leu
1               5                   10

<210> SEQ ID NO 9
<211> LENGTH: 10
<212> TYPE: PRT
<213> ORGANISM: Bos taurus

<400> SEQUENCE: 9

His Pro Glu Tyr Ala Val Ser Val Leu Leu
1               5                   10

<210> SEQ ID NO 10
<211> LENGTH: 10
<212> TYPE: PRT
<213> ORGANISM: Bos taurus

<400> SEQUENCE: 10

Lys Cys Cys Thr Glu Ser Leu Val Asn Arg
1               5                   10

```
<210> SEQ ID NO 11
<211> LENGTH: 9
<212> TYPE: PRT
<213> ORGANISM: Bos taurus

<400> SEQUENCE: 11

Cys Cys Thr Glu Ser Leu Val Asn Arg
1               5

<210> SEQ ID NO 12
<211> LENGTH: 9
<212> TYPE: PRT
<213> ORGANISM: Bos taurus

<400> SEQUENCE: 12

Lys Cys Cys Thr Glu Ser Leu Val Asn
1               5

<210> SEQ ID NO 13
<211> LENGTH: 8
<212> TYPE: PRT
<213> ORGANISM: Bos taurus

<400> SEQUENCE: 13

Cys Cys Thr Glu Ser Leu Val Asn
1               5

<210> SEQ ID NO 14
<211> LENGTH: 11
<212> TYPE: PRT
<213> ORGANISM: Bos taurus

<400> SEQUENCE: 14

Arg Phe Lys Asp Leu Gly Glu Glu His Phe Lys
1               5                   10

<210> SEQ ID NO 15
<211> LENGTH: 10
<212> TYPE: PRT
<213> ORGANISM: Bos taurus

<400> SEQUENCE: 15

Phe Lys Asp Leu Gly Glu Glu His Phe Lys
1               5                   10

<210> SEQ ID NO 16
<211> LENGTH: 10
<212> TYPE: PRT
<213> ORGANISM: Bos taurus

<400> SEQUENCE: 16

Arg Phe Lys Asp Leu Gly Glu Glu His Phe
1               5                   10

<210> SEQ ID NO 17
<211> LENGTH: 9
<212> TYPE: PRT
<213> ORGANISM: Bos taurus

<400> SEQUENCE: 17

Phe Lys Asp Leu Gly Glu Glu His Phe
1               5
```